United States Patent
Sundberg et al.

(10) Patent No.: US 11,285,144 B2
(45) Date of Patent: Mar. 29, 2022

(54) USE OF CDK8 INHIBITORS TO TREAT DISEASES OF INFLAMMATION AND AUTOIMMUNITY

(71) Applicants: THE BROAD INSTITUTE, INC., Cambridge, MA (US); THE GENERAL HOSPITAL CORPORATION, Boston, MA (US); DANA-FARBER CANCER INSTITUTE, INC., Boston, MA (US); PRESIDENT AND FELLOWS OF HARVARD COLLEGE, Cambridge, MA (US)

(72) Inventors: Thomas Sundberg, Cambridge, MA (US); Alykhan Shamji, Cambridge, MA (US); Ramnik Xavier, Boston, MA (US); Liv Johannessen, Boston, MA (US); Nathanael Gray, Boston, MA (US); Bernard Khor, Boston, MA (US); Jose Perez, Cambridge, MA (US)

(73) Assignees: The Broad Institute, Inc., Cambridge, MA (US); The General Hospital Corporation, Boston, MA (US); Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 8 days.

(21) Appl. No.: 16/323,227

(22) PCT Filed: Aug. 3, 2017

(86) PCT No.: PCT/US2017/045387
§ 371 (c)(1),
(2) Date: Feb. 4, 2019

(87) PCT Pub. No.: WO2018/027082
PCT Pub. Date: Feb. 8, 2018

(65) Prior Publication Data
US 2019/0183881 A1    Jun. 20, 2019

Related U.S. Application Data

(60) Provisional application No. 62/510,055, filed on May 23, 2017, provisional application No. 62/370,562, filed on Aug. 3, 2016.

(51) Int. Cl.
| A61K 31/4709 | (2006.01) |
| A61K 31/4725 | (2006.01) |
| G01N 33/68 | (2006.01) |
| A61K 31/4985 | (2006.01) |
| A61K 31/5025 | (2006.01) |
| A61K 31/407 | (2006.01) |
| A61K 31/4545 | (2006.01) |
| A61K 31/44 | (2006.01) |
| A61K 31/444 | (2006.01) |
| A61K 31/517 | (2006.01) |
| A61K 31/58 | (2006.01) |
| A61K 35/17 | (2015.01) |
| A61K 38/00 | (2006.01) |

(52) U.S. Cl.
CPC ........ *A61K 31/4709* (2013.01); *A61K 31/407* (2013.01); *A61K 31/44* (2013.01); *A61K 31/444* (2013.01); *A61K 31/4545* (2013.01); *A61K 31/4725* (2013.01); *A61K 31/4985* (2013.01); *A61K 31/5025* (2013.01); *A61K 31/517* (2013.01); *A61K 31/58* (2013.01); *A61K 35/17* (2013.01); *G01N 33/6869* (2013.01); *A61K 38/00* (2013.01); *Y02A 50/30* (2018.01)

(58) Field of Classification Search
CPC combination set(s) only.
See application file for complete search history.

(56) References Cited

U.S. PATENT DOCUMENTS

| 6,407,103 B2 | 6/2002 | Nugiel et al. |
| 7,868,139 B2 | 1/2011 | Elson et al. |
| (Continued) | | |

FOREIGN PATENT DOCUMENTS

| WO | WO-2007082980 A1 * | 7/2007 | ............ A61K 38/22 |
| WO | 2012092382 A2 | 7/2012 | |
| (Continued) | | | |

OTHER PUBLICATIONS

WO 2007082980 machine translations.*
Pinter, E et al Brit J Pharmacol 2014 vol. 77 pp. 5-20.*
Canning, P. et al, Chem & Biol. 2015 vol. 22, pp. 1174-1184.*
"International Preliminary Report on Patentability issued in International Application No. PCT/US2017/045387 dated Feb. 14, 2019", 9 pages.

(Continued)

*Primary Examiner* — Heidi Reese
(74) *Attorney, Agent, or Firm* — Johnson, Marcou, Isaacs & Nix, LLC; F. Brent Nix, Esq.; Rachel D. Rutledge, Esq.

(57) ABSTRACT

A method for treating inflammation and/or autoimmune diseases comprises administering to a subject in need thereof, a composition comprising a CDK8 inhibitor. In another aspect, a method for increasing IL-10 production comprises administering to a subject in need thereof a CDK8 inhibitor. In another aspect, a method for enhancing $T_{reg}$ cell differentiation, comprising administering a composition comprising a CDK8 inhibitor. In certain example embodiments, the subject suffers from an inflammatory bowel disease. In certain other example embodiments, the subject requires immunosuppression to prevent rejection following a transplantation procedure.

12 Claims, 20 Drawing Sheets

(56) References Cited

U.S. PATENT DOCUMENTS

| | | | |
|---|---|---|---|
| 9,834,541 B2* | 12/2017 | Schiemann | C07D 401/04 |
| 2007/0054916 A1 | 3/2007 | Patel et al. | |

FOREIGN PATENT DOCUMENTS

| | | | |
|---|---|---|---|
| WO | 2013/116786 A1 | 8/2013 | |
| WO | 2014194201 A2 | 12/2014 | |
| WO | WO-2014194201 A2 * | 12/2014 | A61K 31/5377 |
| WO | 2015100420 A1 | 7/2015 | |
| WO | 2018/027082 A1 | 2/2018 | |

OTHER PUBLICATIONS

Yamaoka, Kunihiro, "Janus Kinase Inhibitors for Rheumatoid Arthritis", Current Opinion in Chemical Biology, vol. 32, Jun. 2016, 29-33.

Aikawa, et al., "Treatment of Arthritis with a Selective Inhibitor of C-Fos/Activator Protein-1", Nature Biotechnology, vol. 26, No. 7, Jul. 2008, 817-823.

Allen, et al., "The Mediator Complex: A Central Integrator of Transcription", Nature Reviews Molecular Cell Biology, vol. 16, No. 3, Mar. 2015, 29 pages.

Aoki, et al., "Cortistatins A, B, C, And D, Anti-Angiogenic Steroidal Alkaloids, from The Marine Sponge Corticium Simplex", Journal of the American Chemical Society, vol. 128, No. 10, 2006, 3148-3149.

Asadullah, et al., "Interleukin-10 Therapy review of a New Approach", Pharmacological Reviews, vol. 55, No. 2, Jun. 2003, 241-269.

Bancerek, et al., "CDK8 Kinase Phosphorylates Transcription Factor STAT1 to Selectively Regulate the Interferon Response", Immunity, vol. 38, No. 2, Feb. 21, 2013, 250-262.

Braat, et al., "A Phase I Trial with Transgenic Bacteria Expressing Interleukin-10 in Crohn's Disease", Clinical Gastroenterology and Hepatology, vol. 4, No. 6, Jun. 2006, 754-759.

Clark, et al., "Phosphorylation of CRTC3 By the Salt-inducible Kinases Controls The Interconversion of Classically Activated and Regulatory Macrophages", Proceedings of the National Academy of Sciences of the United States of America, vol. 109, No. 42, | Oct. 16, 2012, 16986-16991.

Clarke, et al., "Assessing the Mechanism and Therapeutic Potential of Modulators of the Human Mediator Complex-associated Protein Kinases", Elife, vol. 5, 2016, 25 pages.

Connell, et al., "Simultaneous Pathway Activity Inference and Gene Expression Analysis Using RNA Sequencing", Cell Systems, vol. 2, May 25, 2016, 323-334.

Donner, "CDK8 is a Positive Regulator of Transcriptional Elongation Within The Serum Response Network", Nature Structural and Molecular Biology, vol. 17, No. 2, Feb. 2010, 22 pages.

Galeazzi, et al., "A Phase IB Clinical Trial with Dekavil (F8-IL10), an Immunoregulatory 'armed Antibody' for the Treatment of Rheumatoid Arthritis, used in Combination Wilh Methotrexate", The Israel Medical Association Journal, vol. 16, No. 10, Oct. 2014, 666 page.

Garber, et al., "A High-Throughput Chromatin Immunoprecipitation Approach Reveals Principles of Dynamic Gene Regulation in Mammals", Molecular Cell, vol. 47, No. 5, Sep. 14, 2012, 19 pages.

Gordon, et al., "CC-10004 but not Thalidomide or Lenalidomide Inhibits Lamina Propria Mononuclear Cell TNF-α and MMP-3 Production in Patients with Inflammatory Bowel Disease", Journal of Crohn's and Colitis, vol. 3, 2009, 175-182.

Herman, et al., "CD4+CD25+ T Regulatory Cells Dependent on ICOS Promote Regulation of Effector Cells in the Prediabetic Lesion", Journal of Experimental Medicine, vol. 199, No. 11, Jun. 7, 2004, 1479-1489.

Itakura, et al., "IL-10 Expression by Primary Tumor Cells Correlates with Melanoma Progression from Radial to Vertical Growth Phase and Development of Metastatic Competence", Modern Pathology, vol. 24, No. 6, Feb. 2011, 801-809.

Khor, et al., "The Kinase DYRK1A Reciprocally Regulates the Differentiation of Th17 and Regulatory T Cells", eLife, vol. 4, No. e05920, 2015, 27 pages.

Kotoku, et al., "Creation of Readily Accessible and Orally Active Analogue of Cortistatin A", ACS Medicinal Chemistry Letters, vol. 3, No. 8, Jul. 10, 2012, 5 pages.

Kwiatkowski, et al., "Targeting Transcription Regulation in Cancer with a Covalent CDK7 Inhibitor", Nature, vol. 511, Jul. 2014, 16 pages.

Li, et al., "Cyclin C is a Haploinsufficient Tumour Suppressor", Nature Cell Biology, vol. 16, No. 11, Nov. 2014, 37 pages.

Lim, et al., "Cdks, Cyclins and CKIS: Roles Beyond Cell Cycle Regulation", Development, vol. 140, 2013, 3079-3093.

Lin, et al., "Casein Kinase Li is a Negative Regulator of C-jun DNA Binding and AP-1 Activity", Cell, vol. 70, No. 5, Sep. 4, 1992, 777-789.

Mallinger, et al., "2,8-Disubstituted-1,6-Naphthyridines and 4,6-Disubstituted-Isoquinolines with Potent, Selective Affinity for CDK8/19", ACS Medicinal Chemistry Letters, vol. 7, No. 6, Mar. 28, 2016, 573-578.

Mallinger, et al., "Discovery of Potent, Selective, and Orally Bioavailable Small-Molecule Modulators of the Mediator Complex-Associated Kinases CDK8 and CDK19", Journal of Medicinal Chemistry, vol. 59, No. 3, Jan. 21, 2016, 1078-1101.

Marlow, et al., "Why Interleukin-10 Supplementation Does Not Work in Crohn's Disease Patients", World Journal of Gastroenterology, vol. 19, No. 25, Jul. 7, 2013, 3931-3941.

Martin, et al., "Toll-Like Receptor-Mediated Cytokine Production is Differentially Regulated by Glycogen Synthase Kinase 3", Nature Immunology, vol. 6, No. 8, Aug. 2005, 16 pages.

Miller, et al., "Identification of Known Drugs that Act as Inhibitors of NF-κB Signaling and their Mechanism of Action", Biochemical Pharmacology, vol. 70, No. 9, May 1, 2010, 23 pages.

Na, et al., "The Early Synthesis of p35 and Activation of CDK5 In LPS-stimulated Macrophages Suppresses Interleukin-10 Production", Science Signaling, vol. 8, No. 404, Nov. 24, 2015, 121 page.

Pelish, et al., "Mediator Kinase Inhibition Further Activates Super-Enhancer-Associated Genes in AML", Nature, vol. 526, No. 7572, Oct. 8, 2015, 32 pages.

Porter, et al., "Cyclin-Dependent Kinase 8 Mediates Chemotherapy-Induced Tumor-Promoting Paracrine Activities", Proceedings of the National Academy of Sciences of the United States of America, vol. 109, No. 34, Aug. 21, 2012, 13799-13804.

Poss, et al., "Identification of Mediator Kinase Substrates in Human Cells using Cortistatin A and Quantitative Phosphoproteomics", Cell Reports, vol. 15, No. 2, Apr. 12, 2016, 436-450.

Pyonteck, et al., "CSF-1R Inhibition Alters Macrophage Polarization and Blocks Glioma Progression", Nature Medicine, vol. 19, No. 10, Oct. 2013, 12 pages.

Rodriguez, et al., "Polarization of the Innate Immune Response by Prostaglandin E2: A Puzzle of Receptors and Signals", Molecular Pharmacology, vol. 85, No. 1, Jan. 2014, 187-197.

Saraiva, et al., "The Regulation of IL-10 Production by Immune Cells", Nature Reviews Immunology, vol. 10, No. 3, Feb. 15, 2010, 13 pages.

Schreiber, et al., "Safety and Efficacy of Recombinant Human Interleukin 10 in Chronic Active Crohn's Disease. Crohn's Disease IL-10 Cooperative Study Group", Gastroenterology, vol. 119, No. 6, 2000, 1461-1472.

Shi, et al., "Scalable Synthesis of Cortistatin A and Related Structures", Journal of the American Chemical Society, vol. 133, No. 20, May 3, 2011, 8014-8027.

Shlyueva, et al., "Transcriptional Enhancers: from Properties to Genome-wide Predictions", Nature Reviews Genetics, vol. 15, No. 4, 2014, 272-286.

Shouval, et al., "Interleukin 10 Receptor Signaling: Master Regulator of Intestinal Mucosal Homeostasis in Mice and Humans", Advances in Immunology, vol. 122, 2014, 29 pages.

Souto, et al., "Apremilast For the Treatment of Psoriatic Arthritis", Expert Review of Clinical Immunology, vol. 11, No. 12, 2015, 1281-1290.

Sundberg, et al., "Small-molecule Screening Identifies Inhibition of Salt-inducible Kinases as a Therapeutic Strategy to Enhance Immunoregulatory Functions of Dendritic Cells", Proceedings of the National Academy of Sciences of the United States of America, vol. 111, No. 34, Aug. 26, 2014, 12468-12473.

(56) References Cited

OTHER PUBLICATIONS

Taira, et al., "DYRK2 Priming Phosphorylation of C-jun and C-Myc Modulates Cell Cycle Progression in Human Cancer Cells", The Journal of Clinical Investigation, vol. 122, No. 3 , Mar. 2012, 859-872.

Tarbell, et al., "CD25+ CD4+ T Cells, Expanded with Dendritic Cells Presenting a Single Autoantigenic Peptide, Suppress Autoimmune Diabetes", Journal of Experimental Medicine, vol. 199, No. 11, Jun. 7, 2004, 1467-1477.

Wang, et al., "Expression of CD163, Interleukin-10, and Interferon-gamma in Oral Squamous Cell Carcinoma: Mutual Relationships and Prognostic Implications", European Journal of Oral Sciences, vol. 122, No. 3, Jun. 2014, 202-209.

Wang, et al., "Microtubule Acetylation Amplifies P38 Kinase Signalling and Anti-inflammatory IL-10 Production", Nature Communications, vol. 5, No. 3479, Mar. 17, 2014, 7 pages.

Witte, et al., "Super-enhancers: Asset Management in Immune Cell Genomes", Trends in Immunology, vol. 36, No. 9, Sep. 2015, 18 pages.

Xing, et al., "Scaffold Mining of Kinase Hinge Binders in Crystal Structure Database", Journal of Computer-Aided Molecular Design, vol. 28, No. 1, Jan. 2014, 13-23.

Yamamoto, et al., "Mediator Cyclin-Dependent Kinases Upregulate Transcription of Inflammatory Genes in Cooperation With Nf-κB and C/Ebpβ on Stimulation of Toll-Like Receptor 9", Genes to Cells, vol. 22, 2017, 265-276.

Copenheaver, "International Search Report and Written Opinion issued in International Application No. PCT/US2017/045387", dated Oct. 24, 2017.

Dale, et al., "A Selective Chemical Probe for Exploring the Role of CDK8 and CDK19 in Human Disease", Nature Chemical Biology, Oct. 26, 2015, vol. 11, No. 12, pp. 973-980.

Elcombe, et al., "Dectin-1 Regulates IL-10 Production via a MSK1/2 and CREB Dependent Pathway and Promotes the Induction of Regulatory Macrophage Markers", PLoS One, Mar. 22, 2013, vol. 8, No. 3; pp. 1-17.

Sidhu, et al., "Small Molecule Tyrosine Kinase Inhibitors for the Treatment of Intestinal Inflammation", Inflammatory Bowel Diseases, Mar. 21, 2011, vol. 17, No. 12, Pos. 2416-2426., 16 pages.

\* cited by examiner

| Analog | Structure | CDK8 IC$_{50}$ (µM) | IL-10 EC$_{50}$ (µM) |
|---|---|---|---|
| BRD-6989 (10) | 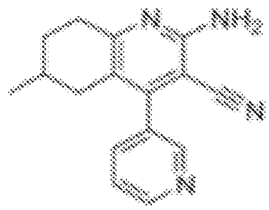 | 0.19 | 1.35 |
| BRD-8408 (11) | 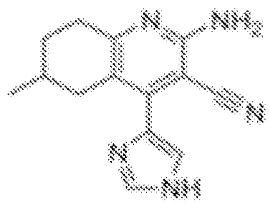 | 1.8 | 19.5 |
| BRD-4054 (12) | 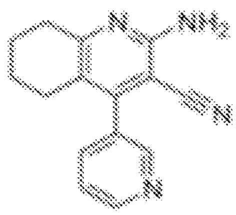 | 2.7 | 16.5 |
| BRD-5817 (13) | 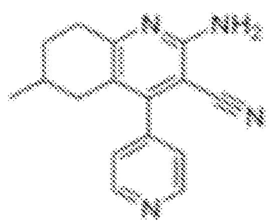 | 30 | 30 |
| BRD-2299 (14) | 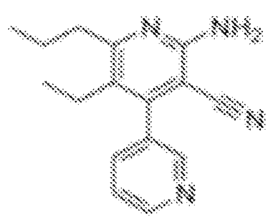 | 43 | 116 |
| BRD-9548 (15) | 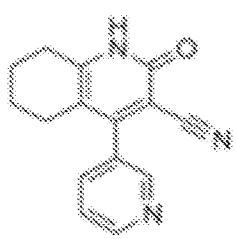 | 147 | 340 |

USE OF CDK8 INHIBITORS TO TREAT DISEASES OF INFLAMMATION AND AUTOIMMUNITY

CROSS-REFERENCE TO RELATED APPLICATIONS

This application is a 35 U.S.C. § 371 national stage application of International Patent Application No. PCT/US2017/045387 filed Aug. 3, 2017, which claims the benefit of U.S. Provisional Application No. 62/370,562 filed Aug. 3, 2016, and U.S. Provisional Application No. 62/510,055 filed May 23, 2017. The entire contents of the above-identified applications are hereby fully incorporated herein by reference.

STATEMENT REGARDING FEDERALLY SPONSORED RESEARCH

This invention was made with government support under grant numbers DK104021, DK062432, and DK043351 granted by the National Institutes of Health. The government has certain rights in the invention.

TECHNICAL FIELD

The subject matter disclosed herein is generally directed to methods for treating inflammatory and/or autoimmune diseases by administering compositions comprising CDK8 inhibitors and/or isolated immune cells differentiated using CDK8 inhibitors.

BACKGROUND

The anti-inflammatory cytokine interleukin-10 (IL-10) promotes immune homeostasis by suppressing inflammatory cytokine production by innate immune cells and by promoting regulatory T cell ($T_{reg}$) function. Genetic studies of inflammatory bowel disease (IBD) have linked single nucleotide polymorphisms (SNPs) near IL-10 to adult-onset IBD and identified rare, loss-of-function mutations in IL-10 or its receptor that result in severe, pediatric-onset enterocolitis. Conversely, IL-10-based therapy reduces disease activity in murine models of colitis, bacterial infection, psoriasis and arthritis, and a fusion protein linking recombinant IL-10 to an inflammation-targeting antibody has shown promise in a clinic trial for rheumatoid arthritis. Hence, while loss of IL-10 function can lead to inflammation, enhancing IL-10 activity may be a viable approach to restore and maintain immune homeostasis.

Small-molecule probes have provided key insights into regulation of IL-10 in innate immune cells. Activators of CREB-dependent transcription such as G protein-coupled receptor agonists or inhibitors of phosphodiesterases (PDEs), salt-inducible kinases (SIKs), or glycogen synthase kinase-3β (GSK-3β) potentiate IL-10 production in macrophages and dendritic cells. Alternatively, amplification of mitogen-activated protein (MAP) kinase signaling by perturbation of microtubule dynamics or inhibition of cyclin-dependent kinase 5 (CDK5) can also up-regulate IL-10. Notably, these probes have identified therapeutically useful drug targets, exemplified by approval of the PDE4 inhibitor apremilast for treatment of psoriatic arthritis as well as pre-clinical evaluation for treatment of IBD. Based on these successes, it was reasoned that unbiased phenotypic screening for small-molecule enhancers of IL-10 production would identify novel mechanisms of IL-10 regulation and, potentially, new targets for development of anti-inflammatory therapies.

In addition, the anti-inflammatory cell type Treg promotes immune homeostasis by suppressing adaptive inflammatory responses. Lack of sufficient Treg is thought to contribute to inflammatory diseases such as Type 1 diabetes and GVHD, and augmenting Treg numbers and function with small molecules is being explored as a therapeutic strategy in a number of contexts.

SUMMARY

In one aspect, a method for treating inflammation and/or autoimmune diseases comprises administering to a subject in need thereof, a composition comprising a CDK8 inhibitor. In another aspect, a method for increasing IL-10 production comprises administering to a subject in need thereof a CDK8 inhibitor. In another aspect, a method for enhancing $T_{reg}$ cell differentiation, comprises administering a composition comprising a CDK8 inhibitor. In certain example embodiments, the subject suffers from an inflammatory bowel disease. In certain other example embodiments, the subject requires immunosuppression to prevent rejection following a transplantation procedure.

In certain example embodiments, IL-10 production is achieved in a CREB-independent manner. In certain other example embodiments, the CDK8 inhibitor modulates innate immune activation, including suppression of NF-κB or STAT1 pathway activity.

In certain example embodiments, the CDK8 inhibitor is a cortistatin, a CCT class CDK8 inhibitor, a senexin, a BRD6989 class CDK8 inhibitor, sorafenib, ponatinib, a 3-benzylindazole, a 6-aza-benzothiophene, 2,8-disubstituted-1,6-naphthyridine, 4,6-disubstituted-isoquinoline, or analogs thereof.

The cortistatin may be cortistatin A, $\Delta^{16}$-cortistatin A, cortistatin J, simplified cortistatin analog, or analogs thereof. The senexin may be senexin A, senexin B, or analogs thereof. The CCT class of CDK8 inhibitors may be CCT251921, CCT251545, or analogs thereof. The BRD6989 class of CDK8 inhibitors may be BRD6989 or analogs thereof.

These and other aspects, objects, features, and advantages of the example embodiments will become apparent to those having ordinary skill in the art upon consideration of the following detailed description of illustrated example embodiments.

DETAILED DESCRIPTION OF THE EXAMPLE EMBODIMENTS

General Definitions

Figure 1:
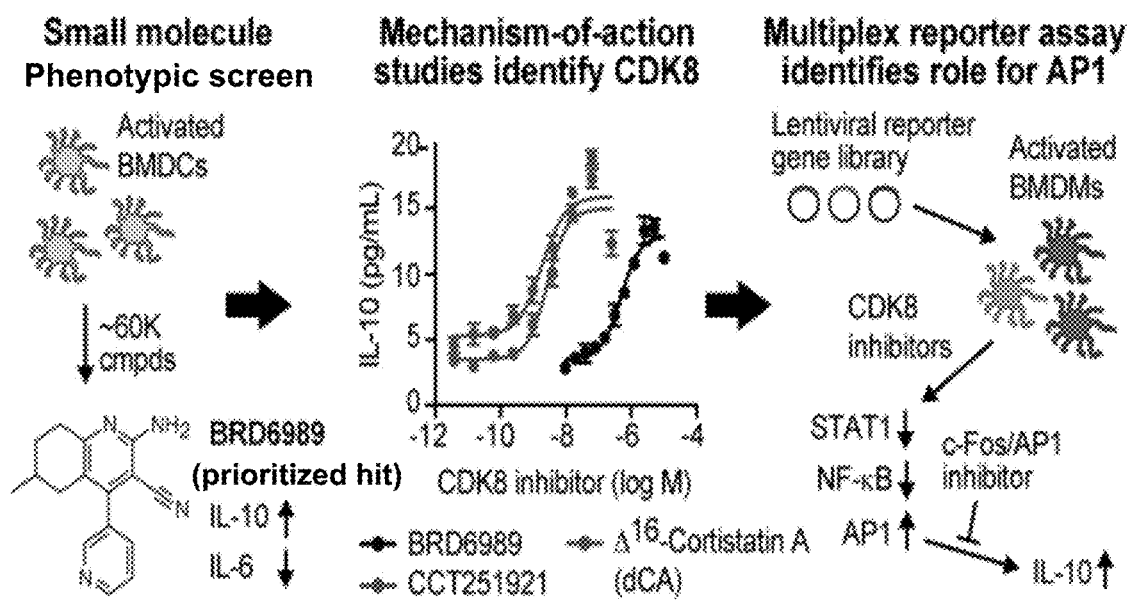
FIG. 1—provides a schematic of an example process for identifying CDK8 inhibitors.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2$^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods for treating inflammation and/or autoimmune diseases by administering compositions comprising CDK8 inhibitors. As demonstrated herein, CDK8 inhibition provides a mechanism to at least enhance IL-10 production that is distinct from previously described regulatory pathways. For example, while modulating cAMP/CREB signaling with small molecules is a proven strategy to up-regulate IL-10, effects on glucose metabolism may complicate therapeutic development of CREB enhancers (24). As further demonstrated herein, targeted CDK8 inhibition appears to have specific and physiologically coherent effects on transcription and therefore may be tolerated without introducing liabilities that may typically result from targeting transcriptional regulatory kinases. Thus, the methods disclosed herein provide a therapeutic strategy for treating diseases and disorders where aberrant activation of innate immune cells contributes to pathology.

As used herein, the term "treating" or "treatment" refers to a complete reversal or elimination of an underlying disease or disorder, a temporary or sustained prevention of a disease or disorder, a temporary or sustained regression of a disease or disorder, and/or amelioration of one or more symptoms associated with a disease or disorder.

Methods of Treatment Using CDK8 Inhibitors

In one aspect, the present invention is directed to a method for treating an inflammatory condition comprising administering a CDK8 inhibitor to a subject in need thereof. Thus, the methods disclosed herein may be used to treat an inflammatory disease/or disorder or an inflammatory condition associated with a certain disease or disorder.

Example inflammatory conditions that may be treated using CDK8 inhibitors include, but are not limited to, Type 1 diabetes graft-versus-host disease, inflammatory bowel disease, psoriasis, psoriatic arthritis, Hashimoto's thyroiditis, food allergy, HCV vasculitis, alopecia areata, systemic lupus erythematosus, multiple sclerosis, and rheumatoid arthritis. In certain example embodiments, the subject suffers from an inflammatory bowel disease such as Crohn's disease or ulcerative colitis.

In another aspect, the present invention is directed to a method for treating autoimmune diseases comprising administering a CDK8 inhibitor to a subject in need thereof. Example autoimmune diseases that may be treated using the methods described herein include, but are not limited to, Addison's disease, agammaglobulinemia, alopecia areata, amyloidosis, ankylosing spondylitis, anti-GBM/anti-TBM nephritis, antiphospholipid syndrome, autoimmune hepatitis, autoimmune inner ear disease, axonal & neuronal neuropathy, Behcet's disease, bullous pemphigoid, Castleman disease, celiac disease, Chagas disease, chronic inflammatory demyelinating polyneuropathy (CIDP), chronic recurrent multifocal osteomyelitis, Churg-Strauss, cicatricial pemphigoid benign mucosal pemphigoid, Cogan's syndrome, cold agglutinin disease, congenital heart block, coxsackie myocarditis, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, Grave's disease, Guillian-Barre syndrome, Hashimoto's thyroiditis, hemolytic anemia, Henoch-Schonlein purpura, herpes gestationis or pemphigold gestationis, hypogammaglobulinemia, IgA nephropathy, IgG4-related sclerosing disease, inclusion body myositis, interstitial cystitis, juvenile arthritis, juvenile diabetes (Type 1 diabetes), juvenile myositis, Kawasaki disease, Lambert-Eaton syndrome, leukocytoclastic vasculitis, lichen planus, lichen sclerosis, ligneous conjunctivitis, linear IgA disease, lupus, lyme disease, chronic Meniere's disease, microscopic polyangiitis, mixed connective tissue disease, Mooren's ulcer, Mucha-Habermann disease, multiple sclerosis, myasthenia gravis, myositis, narcolepsy, neuromyelitis optica, neutropenia, ocular cicatrical pemphigoid, optic neuritis, palindromic rheumatism, PANDAS (pediatric autoimmune neuropsychiatric disorders associated with *Streptococcus*), paraneoplastic cerebellar degeneration, paroxysmal nocturnal hemoglobinuria, Parry Romberg syndrome, pars planitis (peripheral uveitis), Parsonage-Turner syndrome, pemphigus, peripheral neuropathy, perivenous encephalomyelitis, pernicious anemia, POEMS syndrome, polyarteritis nodosa, polymyalgia rheumatic, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, Reiter's syndrome, relapsing polychondritis, restless leg syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, Takayasu's arteritis, temporal arteritis/giant cell arteritis, thrombocytopenic purpura, Tolosa-Hunt syndrome, transverse myelitis, ulcerative colitis, undifferentiated connective tissue disease, uveitis, vasculitis, vitiligo, and Wegner's granulomatosis (granulomatosis with polyangiitis).

In another aspect, the present invention is directed to a method for increasing IL-10 production comprising administering a composition comprising a CDK8 inhibitor to a subject in need thereof. In certain example embodiments, the IL-10 production is increased in a CREB-independent manner.

In another aspect, the present invention is directed to a method for enhancing $T_{reg}$ cell differentiation comprising administering a composition comprising a CDK8 inhibitor to a subject in need thereof.

In another aspect, the present invention is directed to methods for generating $T_{reg}$ cells from naïve precursor cells comprising culturing naïve precursors cells in the presence of one or more CDK8 inhibitors disclosed herein to promote differentiation into functional $T_{reg}$ cells. The nave precursor cells may be derived from an in vitro cell line or may be isolated from a subject and cultured ex vivo. The isolated nave CD4+ cells may be autologous, syngeneic, allogeneic, xenogeneic, or a combination thereof.

The isolated $T_{reg}$ cells may be administered to a subject in need thereof to treat an inflammatory or autoimmune condition, such as those disclosed herein. In other example embodiments, the isolated $T_{reg}$ cells may be administered to restore balance between pro-inflammatory (e.g. Th1 and Th17) and anti-inflammatory (e.g. $T_{regs}$) CD4+ cell lineages to a subject in need thereof.

In certain example embodiments, the compositions described herein are administered to a subject that suffers from an inflammatory condition or autoimmune condition disclosed herein, but does not suffer from cancer.

In another aspect, the claims are directed to a method of immunosuppression following transplantation comprising administering a composition comprising a CDK8 inhibitor to a subject in need thereof.

CDK8 Inhibitors

The compositions discussed above comprise at least one CDK8 inhibitor. In certain example embodiments, the CDK8 inhibitor may increase expression or up-regulate IL-10 and/or modulate innate immune activation including, but not limited to, suppression of NF-κB or STAT1 pathway activity. In certain example embodiments, the CDK8 inhibitor may be a cortistatin or analog thereof, a CCT class CDK8 inhibitor or analog thereof, a senexin or analog thereof, a BRD6989 class CDK8 inhibitor or analog thereof, sorafenib or an analog thereof, ponatinib or an analog thereof, a 2,8-disubstituted-1,6-naphthyridine or analog thereof, a 4,6-disubstituted-isoquinoline or analog thereof, a 3-benzylindazole or analog thereof, a 6-aza-benzothiophene or analog thereof, or a combination thereof.

1. Cortistatins

In certain example embodiments the CDK8 inhibitor is cortistatin type CDK8 inhibitor or an analog thereof. Cortistatins are a group of steroidal alkaloids isolated from the marine sponge *Corticium simplex*. See, e.g. Aoki et al. *JACS* (2006) 128:3148-9. Example cortistatins include cortistatin A (*J. Am. Chem. Soc.* 2011, 133, 8014-80127; *Nature*, 2015 526(7572):273-6), $\Delta^{16}$ cortistatin A (dCA) (*J. Am. Chem. Soc.* 2011, 133:814-8027), cortistatin J (*J. Am. Chem. Soc.* 2011, 133, 8014-827), and simplified cortistatin analog (*ACS Med Chem Lett*. 2012, 3(8):673-677). Structures of cortistatin A, $\Delta^{16}$-cortistatin A, cortistatin J, and simplified cortistatin analog are shown below.

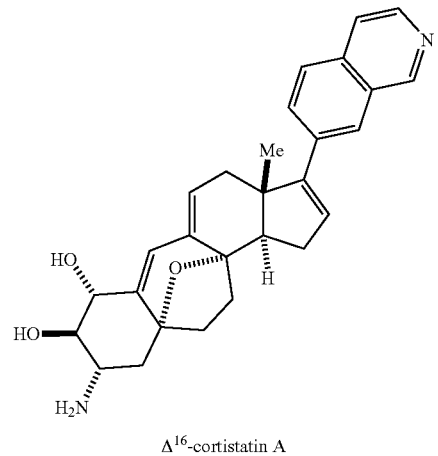

$\Delta^{16}$-cortistatin A

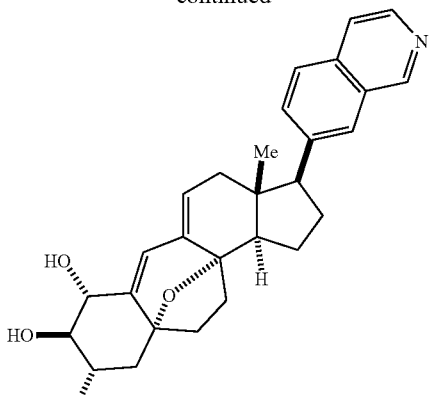

cortistatin A

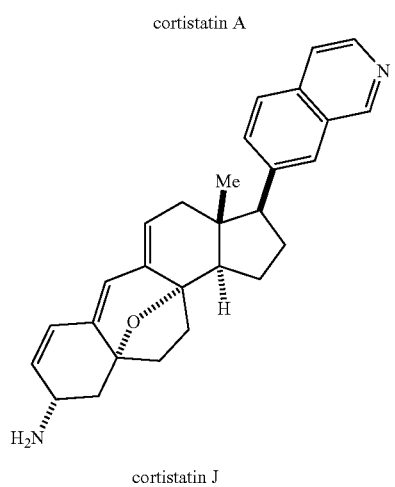

cortistatin J

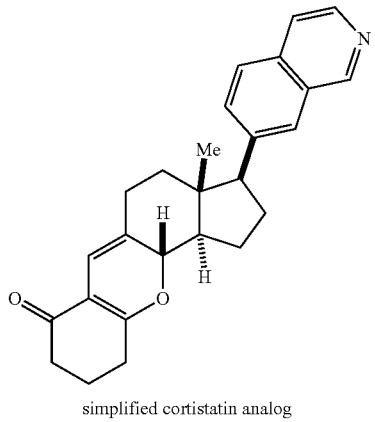

simplified cortistatin analog

2. CCT Class of CDK8 Inhibitors

In certain example embodiments, the CDK8 inhibitor is a CCT class CDK8 inhibitor or an analog thereof. Representative CCT class CDK8 inhibitors include, for example, CCT251921 (*J. Med. Chem.* 2016, 59(3):1078-101), CCT251545 (*Nat Chem Biol.* 2015, 11(12):973-80), 51 (*ACS Med. Chem. Lett.* 2016, 7:573-578), or a combination thereof. In certain example embodiments, the CDK8 inhibitor is CCT251921 or an analog thereof. In certain other example embodiments, the CDK8 inhibitor is CCT251545 or an analog thereof. In certain other example embodiments, the CDK8 inhibitor is "51" or an analog thereof. Representative structures of CCT251921, CCT251545, and 51 are shown below.

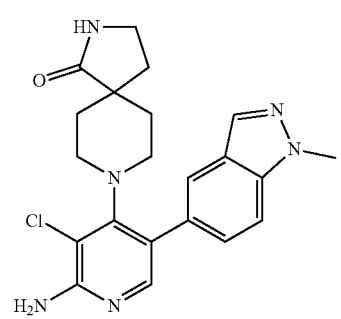

CCT251921

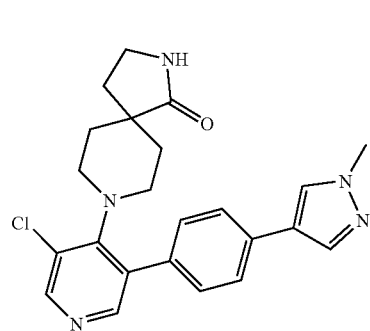

CCT251545

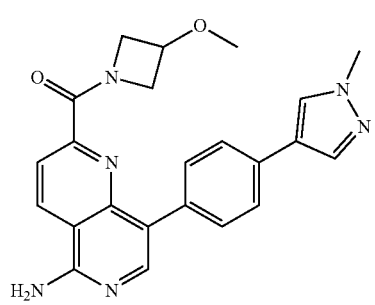

51

3. Senexins

In certain other example embodiments, the CDK8 inhibitor is a senexin CDK8 inhibitor or an analog thereof. Representative senexins include, for example, senexin A (*Proc Natl Acad Sci U.S. Pat. No.* 2,012,109(34):13799-804) and senexin B (International Patent Application Publication No. WO/2013116786). In certain example embodiments, the CDK8 inhibitor is senexin A or an analog thereof. In certain other example embodiments, the CDK8 inhibitor is senexin B or an analog thereof. Representative chemical structures of senexin A and senexin B are shown below.

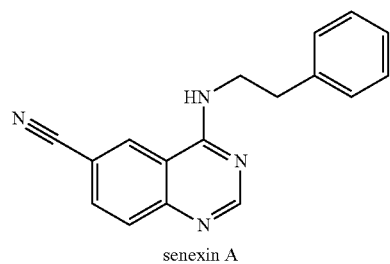

senexin A

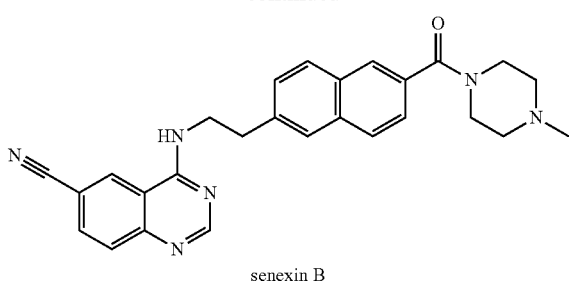

senexin B

4. BRD6989 Class of CDK8 Inhibitors

In certain example embodiments, the CDK8 inhibitor comprises a pyridinyl tetrahydroquinoline core. In certain example embodiments, the CDK8 inhibitor is BRD6989 or an analog thereof. Chemical structures of BRD6989 shown below.

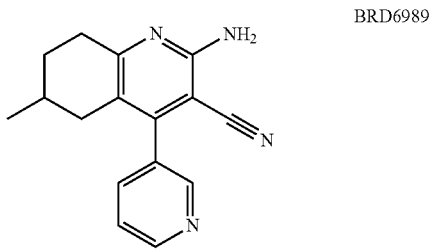 [SMILES: CC1CCc2nc(N)c(C#N)c(-c3cccnc3)c2C1]

BRD6989

5. Other Classes of CDK8 Inhibitors

In certain example embodiments, the CDK8 inhibitor may be sorafenib or a structural analog thereof. Representative structural compounds of sorafenib are shown in compound 1 and compound 20 below.

Compound 1

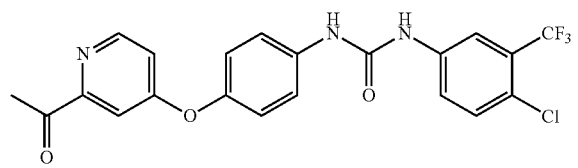

CDK8 IC50 = 32.5 nM
Inhibits 10/220 kinases > 50%
At 0.1 µM.

Compound 20

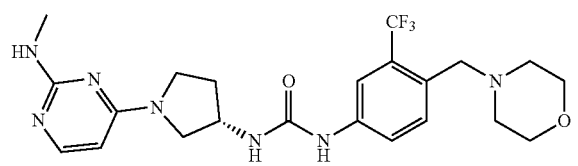

CDK8 IC50 = 17.4 nM
Inhibits 2/220 kinases > 50%
At 0.1 µM.

In certain other example embodiments, the CDK8 inhibitor may be ponatinib and structural analogs thereof. A representative structural of ponatinib is shown below.

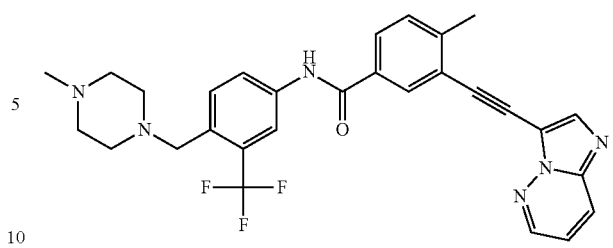

In certain other example embodiments, the CDK8 inhibitor is 2,8-disubstituted-1,6-naphthyridine and/or 4,6-disubstituted-isoquinolines or structural analogs thereof. A representative chemical structure is shown below.

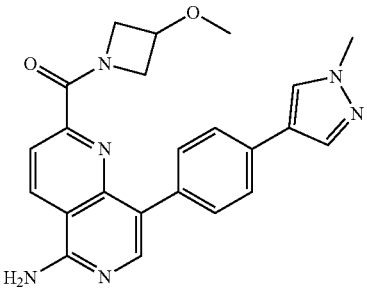 [SMILES: COC1CN(C(=O)c2ccc3c(N)ncc(-c4ccc(-c5cnn(C)c5)cc4)c3n2)C1]

In certain example embodiments, the CDK8 inhibitor is 3-benzylindazole or structural analogs thereof. A representative chemical structure is shown below.

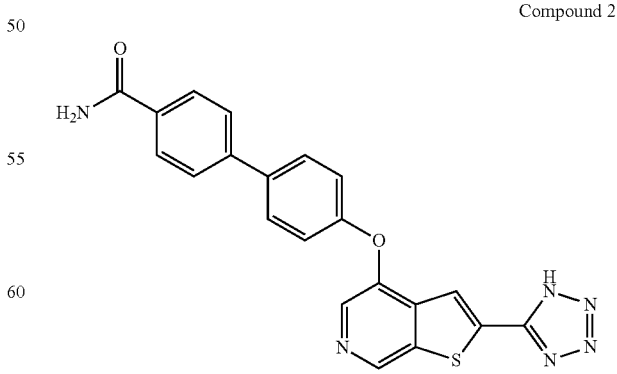

In certain other example embodiments, the CDK8 inhibitor is 6-aza-benzothiophene containing compound or structural analog thereof.

Compound 2

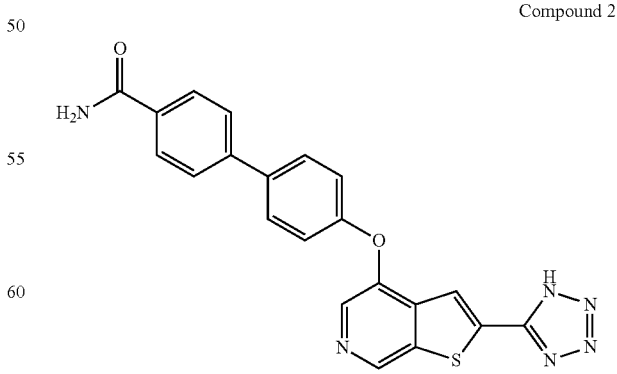

CDK8 IC$_{50}$ = 3 nM
Inhibits 12/51 kinases > 50%
at 0.1 µM

Compound 32

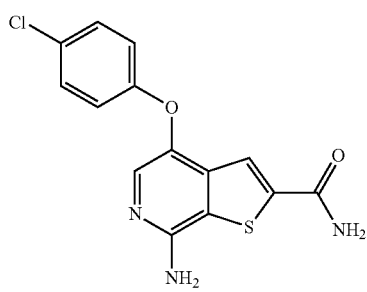

CDK8 $IC_{50}$ = 1.5 nM
Inhibits 11/209 kinases > 50%
at 1 µM

Pharmaceutical Compositions and Administration

While it is possible for the compounds of the present invention to be administered alone, it is preferable to formulate them into a pharmaceutical composition in accordance with standard pharmaceutical practice. Pharmaceutically acceptable excipients are well known in the pharmaceutical art, and are described, for example, in Remington's Pharmaceutical Sciences, $15^{th}$ Ed., Mack Publishing Co., New Jersey (1975). The pharmaceutical excipient can be selected with regard to the intended route of administration and standard pharmaceutical practice. The excipient must be acceptable in the sense of not being deleterious to the recipient thereof.

Pharmaceutically useful excipients that may be used in the formulation of the pharmaceutical composition of the present invention may comprise, for example, carriers, vehicles, diluents, solvents such as monohydric alcohols such as ethanol, isopropanol and polyhydric alcohols such as glycols and edible oils such as soybean oil, coconut oil, olive oil, safflower oil, cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium stearate, talc, monosaccharides, disaccharides, starch, gelatin, cellulose, methylcellulose, sodium carboxymethyl cellulose, dextrose, hydroxypropyl-β-cyclodextrin, polyvinylpyrrolidone, low melting waxes, and ion exchange resins.

The routes for administration (delivery) of the compounds of the invention include, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropyl cellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

If the compounds of the present invention are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention can be administered intranasally or by inhalation and are conveniently delivered in the form of a dry powder inhaler or an aerosol spray presentation from a pressurized container, pump, spray or nebulizer with the use of a suitable propellant, e.g. dichlorodifluoromethane, trichlorofluoromethane, dichlorotetrafluoroethane, a hydrofluoroalkane such as 1,1,1,2-tetrafluoroethane (HFA134A) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound and a suitable powder base such as lactose or starch.

Alternatively, the compounds of the present invention can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

For application topically to the skin, the compounds of the present invention can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

The compounds of the invention may also be used in combination with other therapeutic agents. When a compound of the invention is used in combination with a second therapeutic agent active against the same disease, the dose of each compound may differ from that when the compound is used alone.

The combinations referred to above may conveniently be presented for use in the form of a pharmaceutical formulation. The individual components of such combinations may be administered either sequentially or simultaneously in separate or combined pharmaceutical formulations by any convenient route. When administration is sequential, either the compound of the invention or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

Isolated Immune Cells

In another aspect, the present invention provides for an isolated population of T cells, specifically $T_{reg}$ cells, that have been differentiated using one or more of the CDK8 inhibitors described herein. In certain example embodiments, the precursor cells may be in vivo cells that are then differentiated in the presence of one or more CDK8 inhibitors described herein. In another example embodiments, the isolated population of T cells, may derive from a population of T cells or T cell precursors derived from a patient and then differentiated ex vivo in the presence of one or more CDK8 inhibitors as disclosed herein. In certain example embodiments, the precursor cell is a nave CD4+ T cell. The precursors cells may be autologous, syngeneic, allogeneic, xenogeneic or a combination thereof.

The isolated population may comprise greater than approximately 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or approximately 100% $T_{reg}$ cells.

The terms "isolating" or "isolated" as used throughout this specification with reference to a particular component of a composition or mixture encompass processes or techniques whereby such component is separated from one or more or (substantially) all other components of the composition or mixture (e.g. in vitro culture or patient sample). In certain example embodiments, the terms do not require absolute purity. Instead isolating the component will produce a discrete environment in which the abundance of the component relative to one or more or all other components is greater than in the starting composition or mixture. A "discrete environment" may denote a single medium, such as for example a single solution, dispersion, gel, precipitate etc. Isolating the specified immune cells may increase the abundance of the specified immune cells relative to all other cells e.g. relative to other white blood cells, peripheral mononuclear cells, immune cells, antigen presenting cells, or dendritic cells.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of the specified immune cells in, or to isolate the specified immune cells from, a tested object (e.g., a cell population, tissue, organ, organism, or a biological sample of a subject). Such methods allow to detect, quantify or isolate the specified immune cells in or from the tested object (e.g., a cell population, tissue, organ, organism, or a biological sample of a subject) substantially to the exclusion of other cells comprised in the tested object. Such methods may allow to detect, quantify or isolate the specified immune cells with sensitivity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%, and/or with specificity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%. By means of example, at least 40% (by number), for example at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells detected, quantified or isolated by such methods may correspond to the specified immune cells.

The isolated immune cells or immune cell populations as disclosed throughout this specification may be suitably cultured or cultivated in vitro. The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v $CO_2$ and >95% humidity.

The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

Typically, the medium will comprise a basal medium formulation as known in the art. Many basal media formulations (available, e.g., from the American Type Culture Collection, ATCC; or from Invitrogen, Carlsbad, Calif.) can be used, including but not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Leibovitz L-15, DMEM/F-12, Essential Modified Eagle's Medium (EMEM), RPMI-1640, Medium 199, Waymouth's MB 752/1 or Williams Medium E, and modifications and/or combinations thereof. Compositions of basal media are generally known in the art and it is within the skill of one in the art to modify or modulate concentrations of media and/or media supplements as necessary for the cells cultured.

Such basal media formulations contain ingredients necessary for mammalian cell development, which are known per se. By means of illustration and not limitation, these ingredients may include inorganic salts (in particular salts containing Na, K, Mg, Ca, Cl, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g., glucose, sodium pyruvate, sodium acetate), etc.

For use in culture, basal media can be supplied with one or more further components. For example, additional supplements can be used to supply the cells with the necessary trace elements and substances for optimal growth and expansion. Furthermore, antioxidant supplements may be added, e.g., β-mercaptoethanol. While many basal media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds, exemplified but not limited to, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Lipids and lipid carriers can also be used to supplement cell culture media. Such lipids and carriers can include, but are not limited to cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulations.

Also contemplated is supplementation of cell culture media with mammalian plasma or sera. Plasma or sera often contain cellular factors and components that facilitate cell viability and expansion. Optionally, plasma or serum may be heat inactivated. Heat inactivation is used in the art mainly to remove the complement. Heat inactivation typically involves incubating the plasma or serum at 56° C. for 30 to 60 min, e.g., 30 min, with steady mixing, after which the plasma or serum is allowed to gradually cool to ambient temperature. A skilled person will be aware of any common modifications and requirements of the above procedure. Optionally, plasma or serum may be sterilised prior to storage or use. Usual means of sterilisation may involve, e.g., filtration through one or more filters with pore size smaller than 1 µm, preferably smaller than 0.5 µm, e.g., smaller than 0.45 µm, 0.40 µm, 0.3 5 µm, 0.30 µm or 0.25 µm, more preferably 0.2 µm or smaller, e.g., 0.15 µm or smaller, 0.10 µm or smaller. Suitable sera or plasmas for use in media as taught herein may include human serum or plasma, or serum or plasma from non-human animals, preferably non-human mammals, such as, e.g., non-human primates (e.g., lemurs, monkeys, apes), foetal or adult bovine, horse, porcine, lamb, goat, dog, rabbit, mouse or rat serum or plasma, etc., or any combination of such. In certain preferred embodiments, a medium as taught herein may comprise bovine serum or plasma, preferably foetal bovine (calf) serum or plasma, more preferably foetal bovine (calf) serum (FCS or FBS). When culturing human cells, media may preferably comprise human serum or plasma, such as autologous or allogeneic human serum or plasma, preferably human serum, such as autologous or allogeneic human serum, more preferably autologous human serum or plasma, even more preferably autologous human serum.

In certain preferred embodiments, serum or plasma can be substituted in media by serum replacements, such as to provide for serum-free media (i.e., chemically defined media). The provision of serum-free media may be advantageous particularly with view to administration of the media or fraction(s) thereof to subjects, especially to human subjects (e.g., improved bio-safety). By the term "serum replacement" it is broadly meant any a composition that may be used to replace the functions (e.g., cell maintenance and growth supportive function) of animal serum in a cell culture medium. A conventional serum replacement may typically comprise vitamins, albumin, lipids, amino acids, transferrin, antioxidants, insulin and trace elements. Many commercialized serum replacement additives, such as KnockOut Serum Replacement (KOSR), N2, B27, Insulin-Transferrin-Selenium Supplement (ITS), and G5 are well known and are readily available to those skilled in the art.

Plasma or serum or serum replacement may be comprised in media as taught herein at a proportion (volume of plasma or serum or serum replacement/volume of medium) between about 0.5% v/v and about 40.0% v/v, preferably between about 5.0% v/v and about 20.0% v/v, e.g., between about 5.0% v/v and about 15.0% v/v, more preferably between about 8.0% v/v and about 12.0% v/v, e.g., about 10.0% v/v.

To induce $T_{reg}$ differentiation, the culture media may further comprise, in addition to the components noted above, one or more of the CDK8 inhibitors disclosed herein. The CDK8 inhibitor may be added to the culture media at a concentration of 1 nm-1 µm, 1 nm-900 nm, 1 nm-800 nm, 1 nm-700 nm, 1 nm-600 nm, 1 nm-500 nm, 1 nm-400 nm, 1 nm-300 nm, 1 nm-200 nm, 1 nm-100 nm, 1 nm-90 nm, 1 nm-80 nm, 1 nm-70 nm, 1 nm-60 nm, 1 nm-50 nm, 1 nm-40 nm, 1 nm-30 nm, 1 nm-20 nm, 1 nm-10 nm, 100 nm-1 µm, 100 nm-900 nm, 100 nm-800 nm, 100 nm-700 nm, 100 nm-600 nm, 100 nm-500 nm, 100 nm-400 nm, 100 nm-300 nm, 100 nm-200 nm, 100 nm-190 nm, 100 nm-180 nm, 100 nm-170 nm, 100 nm-160 nm, 100 nm-150 nm, 100 nm-140 nm, 100 nm-130 nm, 100 nm-120 nm, 100 nm-110 nm, 100 nm-105 nm, 125 nm-175 nm, 150 nm-200 nm, 200 nm-1 µm, 200 nm-900 nm, 200 nm-800 nm, 200 nm-700 nm, 200 nm-600 nm, 200 nm-500 nm, 200 nm-400 nm, 200 nm-300 nm, 200 nm-290 nm, 200 nm-280 nm, 200 nm-270 nm, 200 nm-260 nm, 200 nm-250 nm, 200 nm-240 nm, 200 nm, 230 nm, 200 nm-220 nm, 200 nm-210 nm, 200 nm-205 nm, 225 nm-275 nm, 250 nm-300 nm, 300 nm-1 μm, 300 nm-900 nm, 300 nm-800 nm, 300 nm-700 nm, 300 nm-600 nm, 300 nm-500 nm, 300 nm-400 nm, 300 nm-390 nm, 300 nm-380 nm, 300 nm-370 nm, 300 nm-360 nm, 300 nm-350 nm, 300 nm-340 nm, 300 nm-330 nm, 300 nm-320 nm, 300 nm-310 nm, 300 nm-305 nm, 325 nm-375 nm, 350 nm-400 nm, 400 nm-1 μm, 400 nm-900 nm, 400 nm-800 nm, 400 nm-700 nm, 400 nm-600 nm, 400 nm-500 nm, 400 nm-490 nm, 400 nm-480 nm, 400 nm-470 nm, 400 nm-460 nm, 400 nm-450 nm, 400 nm-440, 400 nm-430 nm, 400 nm-420 nm, 400 nm-410 nm, 400 nm-405 nm, 425 nm-475 nm, 450 nm-500 nm, 500 nm-1 μm, 500 nm-900 nm, 500 nm-800 nm, 500 nm-700 nm, 500 nm-600 nm, 500 nm-590 nm, 500 nm-580 nm, 500 nm-570 nm, 500 nm-560 nm, 500 nm-550 nm, 500 nm-540 nm, 500 nm-530 nm, 500 nm-520 nm, 500 nm-510 nm, 500 nm-505 nm, 525 nm-575 nm, 500 nm-600 nm, 600 nm-1 μm, 600 nm-900 nm, 600 nm-800 nm, 600 nm-700 nm, 600 nm-690 nm, 600 nm-680 nm, 600 nm-670 nm, 600 660 nm, 600 650 nm, 600 640 nm, 600 nm-630 nm, 600 nm-620 nm, 600 nm-610 nm, 600 nm-605 nm, 625 nm-675 nm, 650 nm-700 nm, 700 nm-1 μm, 700 nm-900 nm, 700 nm-800 nm, 700 nm-790 nm, 700 nm-780 nm, 700 nm-770 nm, 700 nm-760 nm, 700 nm-750 nm, 700 nm-740 nm, 700 nm-730 nm, 700 nm-720 nm, 700 nm-710 nm, 700 nm-705 nm, 725 nm-775 nm, 750 nm-800 nm, 800 nm-1 μm, 800 nm-900, 800 nm-890 nm, 800 nm-880 nm, 800 nm-870 nm, 800 nm-860 nm, 800 nm-850 nm, 800 nm-840 nm, 800 nm-830 nm, 800 nm-820 nm, 800 nm-810 nm, 800 nm-805 nm, 825 nm-875 nm, 850 nm-900 nm, 900 nm-1 μm, 900 nm-990 nm, 900 nm-980 nm, 900 nm-970 nm, 900 nm-960 n, 900 nm-950 nm-900 nm-940 nm, 900 nm-930 nm, 900 nm-920 nm, 900 nm-910 nm, 900 nm-905 nm. One of ordinary skill can select the appropriate dosage range based on the number of cells to be cultured and CDK8 inhibitor used and extrapolate from the information provided herein. In certain example embodiments, the concentration of CDK8 inhibitor used should be within a range that is consistent with the CDK8 inhibitor's biochemical activity, for example the IC50's for CDK8 inhibition. In certain example embodiment the CDK8 inhibitor is DCA, CCT251921 or a combination thereof.

In certain embodiments, methods for detecting, quantifying or isolating the specified immune cells may be single-cell-based, i.e., may allow to discretely detect, quantify or isolate the specified immune cells as individual cells. In other embodiments, methods for detecting, quantifying or isolating the specified immune cells may be cell population-based, i.e., may only allow to detect, quantify or isolate the specified immune cells as a group or collection of cells, without providing information on or allowing to isolate individual cells.

Methods for detecting, quantifying or isolating the specified immune cells may employ any of the above-described techniques for measuring markers, insofar the separation or the qualitative and/or quantitative measurement of the marker(s) can be correlated with or translated into detection, quantification or isolation of the specified immune cells. For example, any of the above-described biochemical assay methods, immunological assay methods, mass spectrometry analysis methods, chromatography methods, or nucleic acid analysis method, or combinations thereof for measuring markers, may be employed for detecting, quantifying or isolating the specified immune cells.

In certain embodiments, the cells are detected, quantified or isolated using a technique selected from the group consisting of flow cytometry, fluorescence activated cell sorting, mass cytometry, fluorescence microscopy, affinity separation, magnetic cell separation, microfluidic separation, and combinations thereof.

Flow cytometry encompasses methods by which individual cells of a cell population are analyzed by their optical properties (e.g., light absorbance, light scattering and fluorescence properties, etc.) as they pass in a narrow stream in single file through a laser beam. Flow cytometry methods include fluorescence activated cell sorting (FACS) methods by which a population of cells having particular optical properties are separated from other cells.

Elemental mass spectrometry-based flow cytometry, or mass cytometry, offers an approach to analyze cells by replacing fluorochrome-labelled binding reagents with mass tagged binding reagents, i.e., tagged with an element or isotope having a defined mass. In these methods, labeled particles are introduced into a mass cytometer, where they are individually atomized and ionized. The individual particles are then subjected to elemental analysis, which identifies and measures the abundance of the mass tags used. The identities and the amounts of the isotopic elements associated with each particle are then stored and analyzed. Due to the resolution of elemental analysis and the number of elemental isotopes that can be used, it is possible to simultaneously measure up to 100 or more parameters on a single particle.

Fluorescence microscopy broadly encompasses methods by which individual cells of a cell population are microscopically analyzed by their fluorescence properties. Fluorescence microscopy approaches may be manual or preferably automated.

Affinity separation also referred to as affinity chromatography broadly encompasses techniques involving specific interactions of cells present in a mobile phase, such as a suitable liquid phase (e.g., cell population in an aqueous suspension) with, and thereby adsorption of the cells to, a stationary phase, such as a suitable solid phase; followed by separation of the stationary phase from the remainder of the mobile phase; and recovery (e.g., elution) of the adsorbed cells from the stationary phase. Affinity separation may be columnar, or alternatively, may entail batch treatment, wherein the stationary phase is collected/separated from the liquid phases by suitable techniques, such as centrifugation or application of magnetic field (e.g., where the stationary phase comprises magnetic substrate, such as magnetic particles or beads). Accordingly, magnetic cell separation is also envisaged herein.

Microfluidic systems allow for accurate and high throughput cell detection, quantification and/or sorting, exploiting a variety of physical principles. Cell sorting on microchips provides numerous advantages by reducing the size of necessary equipment, eliminating potentially biohazardous aerosols, and simplifying the complex protocols commonly associated with cell sorting. The term "microfluidic system" as used throughout this specification broadly refers to systems having one or more fluid microchannels. Microchannels denote fluid channels having cross-sectional dimensions the largest of which are typically less than 1 mm, preferably less than 500 μm, more preferably less than 400 μm, more preferably less than 300 μm, more preferably less than 200 μm, e.g., 100 μm or smaller. Such microfluidic systems can be used for manipulating fluid and/or objects such as droplets, bubbles, capsules, particles, cells and the like. Microfluidic systems may allow for example for fluorescent label-based (e.g., employing fluorophore-conjugated binding agent(s), such as fluorophore-conjugated antibody(ies)), bead-based (e.g., bead-conjugated binding agent(s), such as bead-conjugated antibody(ies)), or label-free cell sorting (reviewed in Shields et al., Lab Chip. 2015, vol. 15: 1230-1249).

Pharmaceutical Compositions Using Isolated Cells

In another aspect, the present invention provides for a compositions comprising the isolated immune cell population as defined in any embodiment herein. In certain embodiments, the immune cell population may be formulated into a pharmaceutical cell composition.

In certain embodiments, the immune cell or immune cell population is autologous to said subject, i.e., the immune cell or immune cell population is isolated from the same subject as the subject to which/whom the immune cell or immune cell population is to be administered. In certain further embodiments, the immune cell or immune cell population is syngeneic to said subject, i.e., the immune cell or immune cell population is isolated from an identical twin of the subject to which/whom the immune cell or immune cell population is to be administered. In certain further embodiments, the immune cell or immune cell population is allogeneic to said subject, i.e., the immune cell or immune cell population is isolated from a different subject of the same species as the subject to which/whom the immune cell or immune cell population is to be administered. In certain embodiments, the immune cell or immune cell population may even be xenogeneic to said subject, i.e., the immune cell or immune cell population may be isolated from a subject of a different species than the subject to which/whom the immune cell or immune cell population is to be administered.

Preferably, non-autologous, such as allogeneic cells may be selected such as to maximize the tissue compatibility between the subject and the administered cells, thereby reducing the chance of rejection of the administered cells by patient's immune system or graft-vs.-host reaction. For example, advantageously the cells may be typically selected which have either identical HLA haplotypes (including one or preferably more HLA-A, HLA-B, HLA-C, HLA-D, HLA-DR, HLA-DP and HLA-DQ) to the subject, or which have the most HLA antigen alleles common to the subject and none or the least of HLA antigens to which the subject contains pre-existing anti-HLA antibodies.

A "pharmaceutical composition" refers to a composition that usually contains an excipient, such as a pharmaceutically acceptable carrier that is conventional in the art and that is suitable for administration to cells or to a subject.

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatizers, thickeners, agents for achieving a depot effect, coatings, antifungal agents, preservatives, stabilisers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical cell composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the cell-based pharmaceutical composition according to the invention is intended to be used as an infusion. In another example embodiment, the cell-based pharmaceutical composition may be surgically transplanted at or proximate to an inflammatory or autoimmune lesion. The skilled person will understand that compositions which are to be administered orally or topically will usually not comprise cells, although it may be envisioned for oral compositions to also comprise cells, for example when gastrointestinal tract indications are treated. Each of the cells or active components (e.g., immunomodulants) as discussed herein may be administered by the same route or may be administered by a different route. By means of example, and without limitation, cells may be administered parenterally and other active components may be administered orally.

Liquid pharmaceutical cell compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The pharmaceutical cell composition may include one or more cell protective molecules, cell regenerative molecules, growth factors, anti-apoptotic factors or factors that regulate gene expression in the cells. Such substances may render the cells independent of their environment.

Such pharmaceutical cell compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

In certain embodiments, a pharmaceutical cell compositions as taught herein may be administered in a form of liquid composition. In embodiments, the cells or pharmaceutical composition comprising such can be administered systemically, topically, within an organ or at a site of organ dysfunction or lesion.

Preferably, the pharmaceutical cell compositions may comprise a therapeutically effective amount of the specified immune cells and/or other active components (e.g., immunomodulants). The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

The invention is further described in the following examples, which do not limit the scope of the invention described in the claims.

EXAMPLES

Example 1

Enhancing production of the anti-inflammatory cytokine IL-10 is a promising strategy to suppress pathogenic inflammation. To identify new mechanisms regulating IL-10 production, an unbiased phenotypic screen was conducted for small molecules that enhance IL-10 production in activated dendritic cells. Mechanism-of-action (MOA) studies with a prioritized hit from the screen (BRD6989) identified the Mediator-associated kinase CDK8, and its paralog CDK19, as negative regulators of IL-10 production during innate immune activation. The ability of BRD6989 to upregulate IL-10 is recapitulated by multiple, structurally differentiated CDK8/19 inhibitors and requires an intact Cyclin C/CDK8 complex. Using a highly parallel pathway-reporter assay, a role for enhanced AP-1 transcriptional activity in IL-10 potentiation following CDK8/19 inhibition was identified, an effect associated with reduced phosphorylation of a negative regulatory site on c-Jun. These findings identify a role for CDK8/19 in regulating innate immune activation and suggest that these kinases may warrant consideration as therapeutic targets for inflammatory disorders. A graphical representation is shown in FIG. 1.

The anti-inflammatory cytokine interleukin-10 (IL-10) promotes immune homeostasis by suppressing inflammatory cytokine production by innate immune cells and by promoting regulatory T cell (Treg) function (Saraiva et al., Nat Rev Immunol 10:170-81, 2010). Genetic studies of inflammatory bowel disease (IBD) have linked single nucleotide polymorphisms near IL-10 to adult-onset IBD and identified rare, loss-of-function mutations in IL-10 or its receptor that result in severe, pediatric-onset enterocolitis (Shouval et al., Adv Immunol 122:177-210, 2014). Conversely, IL-10-based therapy reduces disease activity in murine models of colitis, bacterial infection, psoriasis and arthritis (Asadullah et al., Pharmacol Rev 55:241-69, 2003). In addition, oral administration of bacteria engineered to express IL-10 or injection of a fusion protein that links recombinant IL-10 (rIL-10) to an inflammation-targeting antibody has shown promise in clinical trials for Crohn's disease and rheumatoid arthritis, respectively (Braat et al., Clin Gastroenterol Hepatol 4:754-9, 2006; Galeazzi et al., Isr Med Assoc J 16:666, 2014). Hence, while impaired IL-10/IL-10R signaling can lead to inflammation, increasing IL-10 abundance may be a viable therapeutic approach to restore and maintain immune homeostasis.

Small-molecule probes have provided key insights into regulation of IL-10 in innate immune cells. Activators of CREB-dependent transcription such as G protein-coupled receptor agonists or inhibitors of phosphodiesterases (PDEs), salt-inducible kinases (SIKs), or glycogen synthase kinase-3β (GSK-3β) potentiate IL-10 production in macrophages and dendritic cells (Rodriguez et al., Mol Pharmacol 85:187-97, 2014; Martin et al., Nat Immunol 6:777-84, 2005; Clark et al., Proc Natl Acad Sci USA 109:16986-91, 2012; Sundberg et al., PNAS 111:12468-12473, 2014). Alternatively, amplification of mitogen-activated protein (MAP) kinase signaling by perturbation of microtubule dynamics or inhibition of cyclin-dependent kinase 5 (CDK5) can also up-regulate IL-10 (Wang et al., Nat Commun 5:3479, 2014; Na et al., Science Signaling 8, 2015). Notably, these probes have identified therapeutically useful drug targets, exemplified by approval of the PDE4 inhibitor apremilast for treatment of psoriatic arthritis as well as pre-clinical evaluation for treatment of IBD (Souto et al., Expert Rev Clin Immunol 11:1281-90, 2015; Gordon et al., J Crohn's & Colitis 3:175-182, 2009). Based on these successes, it was reasoned that unbiased phenotypic screening for small-molecule enhancers of IL-10 production would identify novel mechanisms of IL-10 regulation and, potentially, new targets for development of anti-inflammatory therapies.

Figure 3:
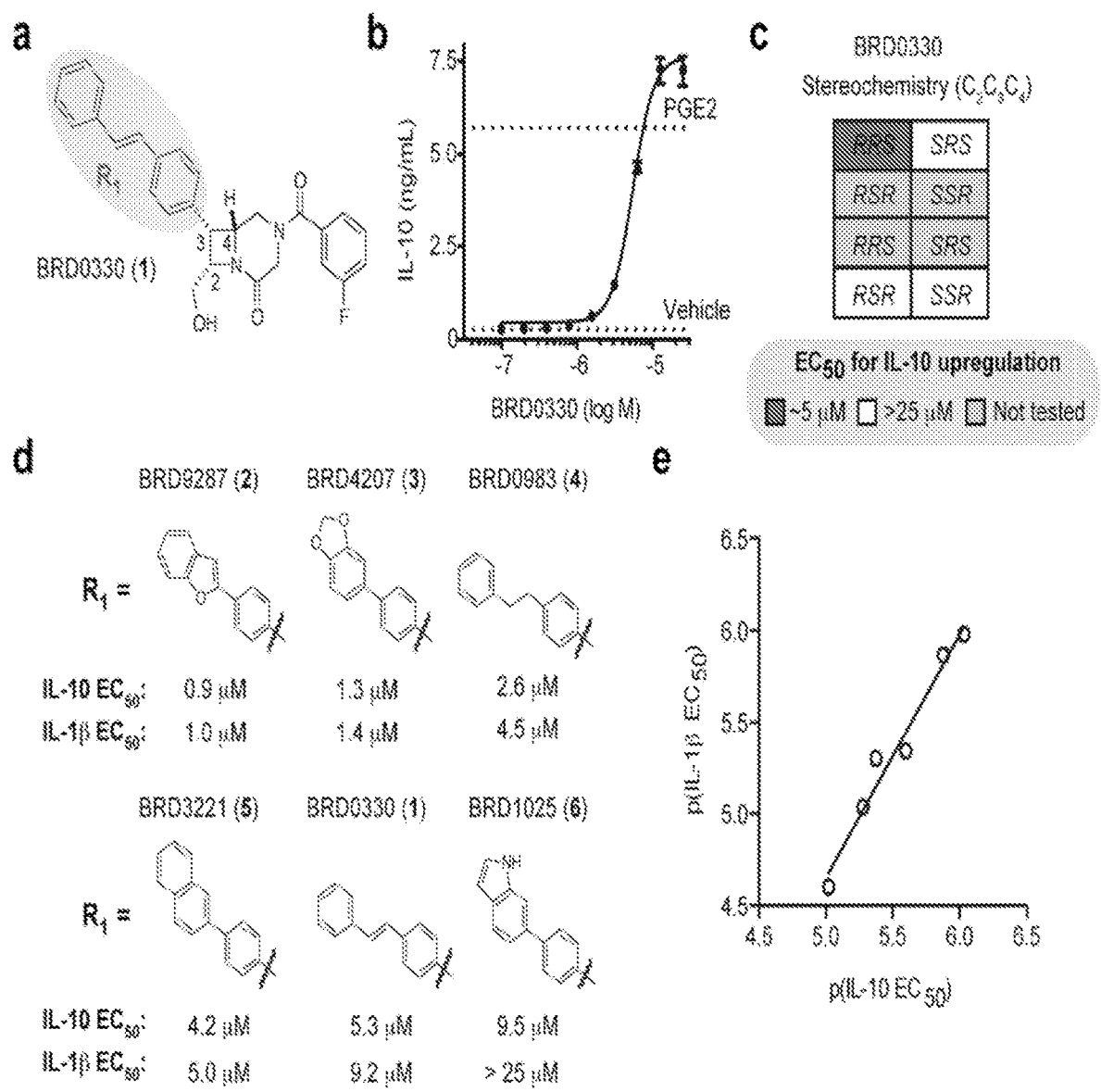
FIG. 3—DOS-derived IL-10 hit BRD0330 was deprioritized due to coordinated upregulation of IL-1β production. (a) Chemical structure of BRD0330. (b) BRD0330 up-regulates IL-10 production by Zymosan A-stimulated BMDCs to a similar extent at PGE2 (each point correspond to mean±S.D.; n=3 biological replicates from 1 independent experiment; data is representative of >4 independent experiments). (c) BRD0330's IL-10 enhancing activity depends on its stereochemistry (EC50's=mean of 2 independent experiments). (d) Substitution of the stilbene side chain (R1) increases potency the potency of IL-10 and IL-1β up-regulation by BRD03330 in activated BMDCs ($EC_{50}$'s are determined from 1 independent experiment). (e) The potency of IL-10 and IL-1β enhancement correlates ($R2=0.97$) for BRD0330 and R1 analogs 2-6.
Figure 4:
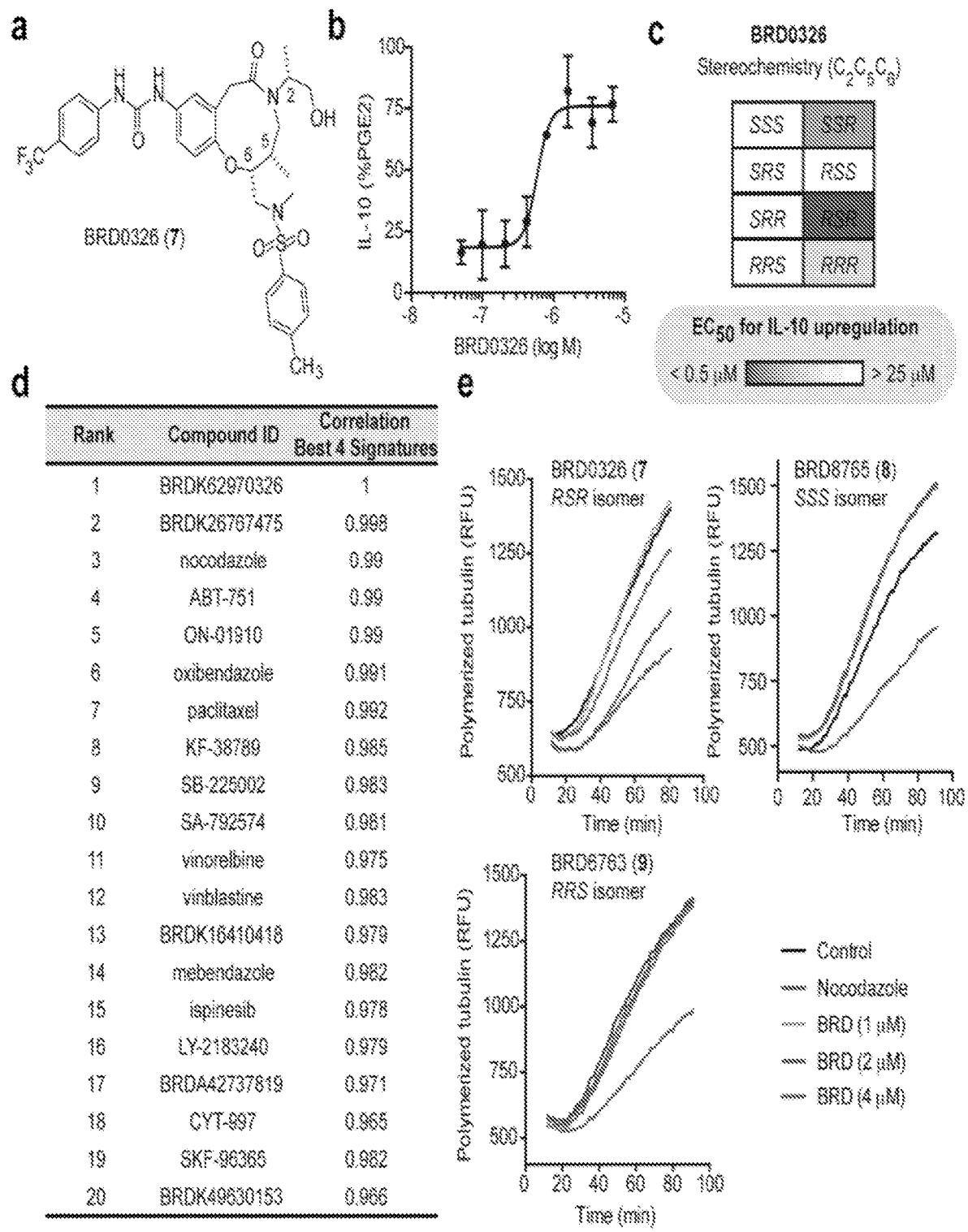
FIG. 4—DOS-derived IL-10 hit BRD0326 perturbs microtubule dynamics. (a) Chemical structure of BRD0326. (b) BRD0326 potentiates IL-10 production by Zymosan A-stimulated BMDCs to a similar degree as PGE2 (each point corresponds to mean±S.D.; n=3 biological replicates from 1 independent experiment; data is representative of 2 independent experiments). (c) BRD0326's IL-10 enhancing activity depends on its stereochemistry ($EC_{50}$'s=mean of 2 independent experiments). (d) Transcriptional responses elicited by BRD0326 correlate with those induced by small molecule modulators of microtubule dynamics. (e) BRD0326, but not the IL-10 inactive stereoisomers BRD8765 or BRD6763, suppresses tubulin polymerization in a cell-free assay (data is from 1 independent experiment).

Identification of Small-Molecule Enhancers of IL-10 Production by Unbiased Phenotypic Screening Towards the goal of identifying new mechanisms of IL-10 regulation, 59,346 small molecules were screened for the ability to enhance IL-10 production by activated bone marrow-derived dendritic cells (BMDCs) using a high-throughput assay developed previously (Sundberg et al., *PNAS* 111:12468-12473, 2014). Compounds were derived from both commercial collections and structurally and skeletally diverse libraries prepared by diversity-oriented synthesis (DOS). More than 60 hit compounds were identified that reproducibly enhance IL-10 production in a concentration-dependent manner (Table 1). Three distinct chemotypes were prioritized for follow-up based on potency and an initial analysis of structure-activity relationship (SAR) with respect to core scaffold, stereochemistry and side chains (FIG. 2a). Among these, the DOS-derived hits BRD0330 (1) and BRD0326 (7) were deprioritized based on data showing that they stimulated production of the inflammatory cytokine IL-1β or suppressed microtubule polymerization, respectively (FIGS. 3 and 4).

TABLE 1

Screening strategy for identification of novel small molecule IL-10 enhancers.

| Category | Parameter | Description |
|---|---|---|
| Assay | Type of assay | Unbiased phenotypic screen for small molecules that up-regulate IL-10 secretion by Zymosan A-stimulated BMDCs. |

TABLE 1-continued

Screening strategy for identification of novel small molecule IL-10 enhancers.

| Category | Parameter | Description |
|---|---|---|
| | Target | Not applicable |
| | Primary measurement | Endogenous IL-10 levels in tissue culture media quantified by AlphaLISA-based assay. |
| | Key reagents | Mouse IL-10 AlphaLISA detection reagent (Perkin Elmer; cat AL502); Zymosan A (Sigma; cat Z4250) |
| | Assay protocol | For detailed description of the high throughput screening protocol, see PNAS 2014 111: 12468-73. |
| | Additional comments | n/a |
| Library | Library size | 59,346 |
| | Library composition | ~47,000 compounds from the Broad Institute's diversity-oriented synthesis library, which is a collection of compounds designed to maximize structural and stereochemical diversity. ~13,000 compounds from commercial screening libraries collected as part of the Molecular Libraries Program. |
| | Source | Broad internal library and various commercial sources. |
| | Additional comments | n/a |
| Screen | Format | 384-well plates |
| | Concentration(s) tested | 25 µM, 0.25% v/v DMSO |
| | Plate controls | Negative control = DMSO; Positive control = PGE2 at final concentration of 5 µM |
| | Reagent/compound dispensing system | BMDCs and Zymosan were dispersed in 384 well plates using a Multidrop Combi Reagent Dispenser (Thermal Scientific) and compounds were pin-transferred using a CyBi-Well Vario (CyBio). |
| | Detection instrument and software | AlphaLISA signal intensity was read using an EnVision multimode plate reader (Perkin Elmer) |
| | Assay validation/QC | Z' > 0.3 for difference between DMSO and PGE2 treated wells |
| | Correction factors | Plate effects were corrected using the Run-based non-parametric algorithm in the Genedata Screener software suite (Genedata). |
| | Normalization | Compound activity was normalized as the percent difference in the IL-10 AlphaLISA signaling in the PGE2-versus DMSO-treated wells on a per plate basis. |
| | Additional comments | n/a |
| Post-HTS analysis | Hit criteria | Hits were classified as compounds that increased IL-10 production by an average of 30% of the PGE2 response from two replicates. |
| | Hit rate | 0.55% (331/59346) |
| | Additional assay(s) | The ability of hit compounds to enhance IL-10 was confirmed by orthogonal techniques including ELISA and cytokine-bead array assays. |
| | Confirmation of hit purity and structure | Compound purity was determined by LC-MS of DMSO stocks used to confirm concentration-dependent enhancement of IL-10 production. BRD-6989 structure and purity was further validated by purchasing powder from a commercial vendor. |
| | Additional comments | n/a |

Prioritized Hit BRD6989 Selectively Upregulates IL-10 by a Distinct Mechanism

Figure 2:
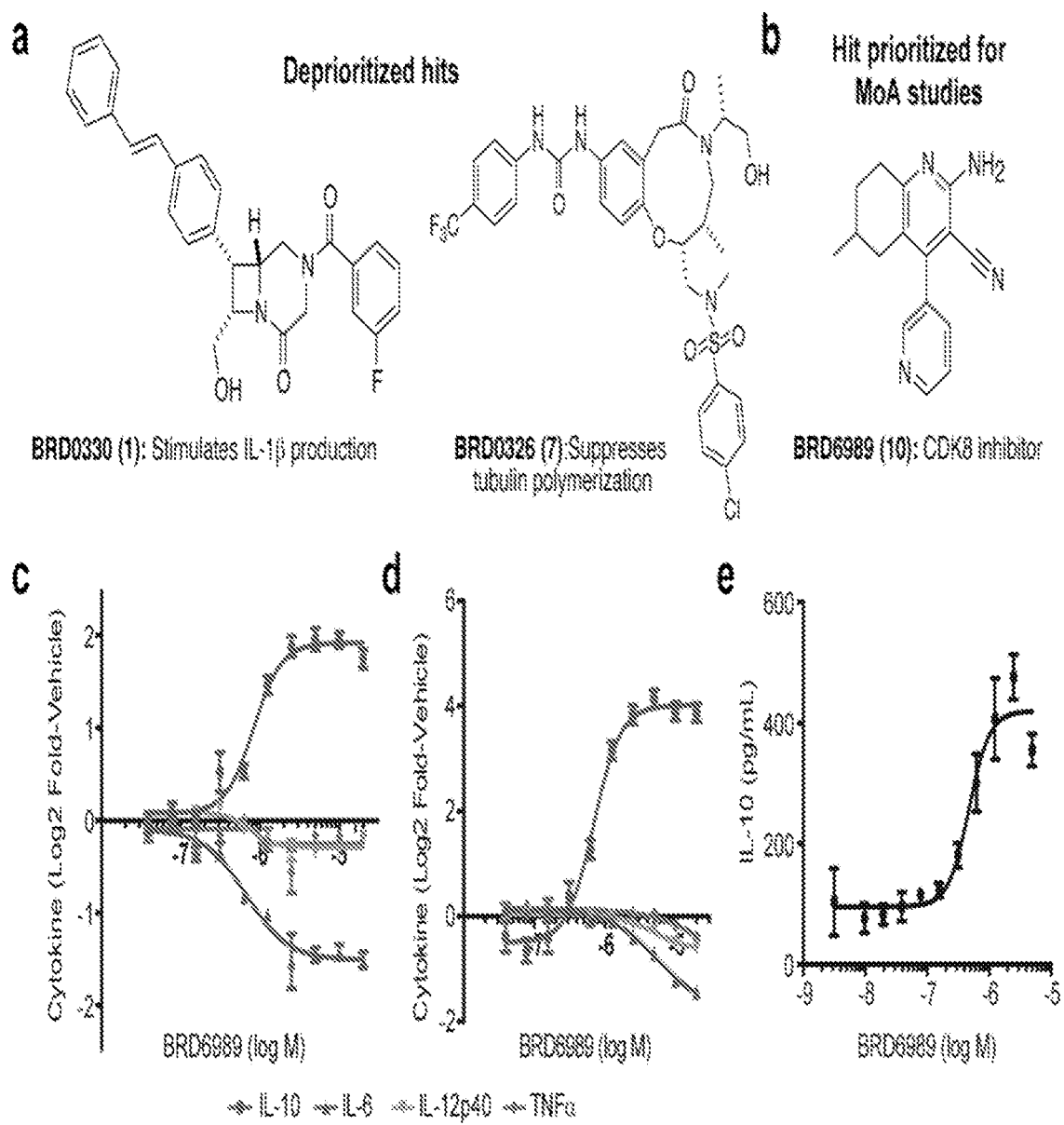
FIG. 2—BRD6989 prioritized from small molecule IL-10 enhancers identified by unbiased phenotypic screening. (a) Chemical structure of IL-10 enhancers identified unbiased phenotypic screening and their rationale for deprioritization. (b) Chemical structure of BRD6989. (c,d) Effect of BRD6989 on cytokine production in BMDCs stimulated with Zymosan A (c) or R848 (d) (each point corresponds to mean±S.D.; n=3 biological replicates from 1 independent experiment). (e) Effect of BRD6989 on IL-10 production in human DCs stimulated with R848 (each point corresponds to mean±S.D.; n=3 biological replicates from 1 independent experiment using cells derived from 1 donor). All data is representative of at least 2 independent experiments.
Figure 5:
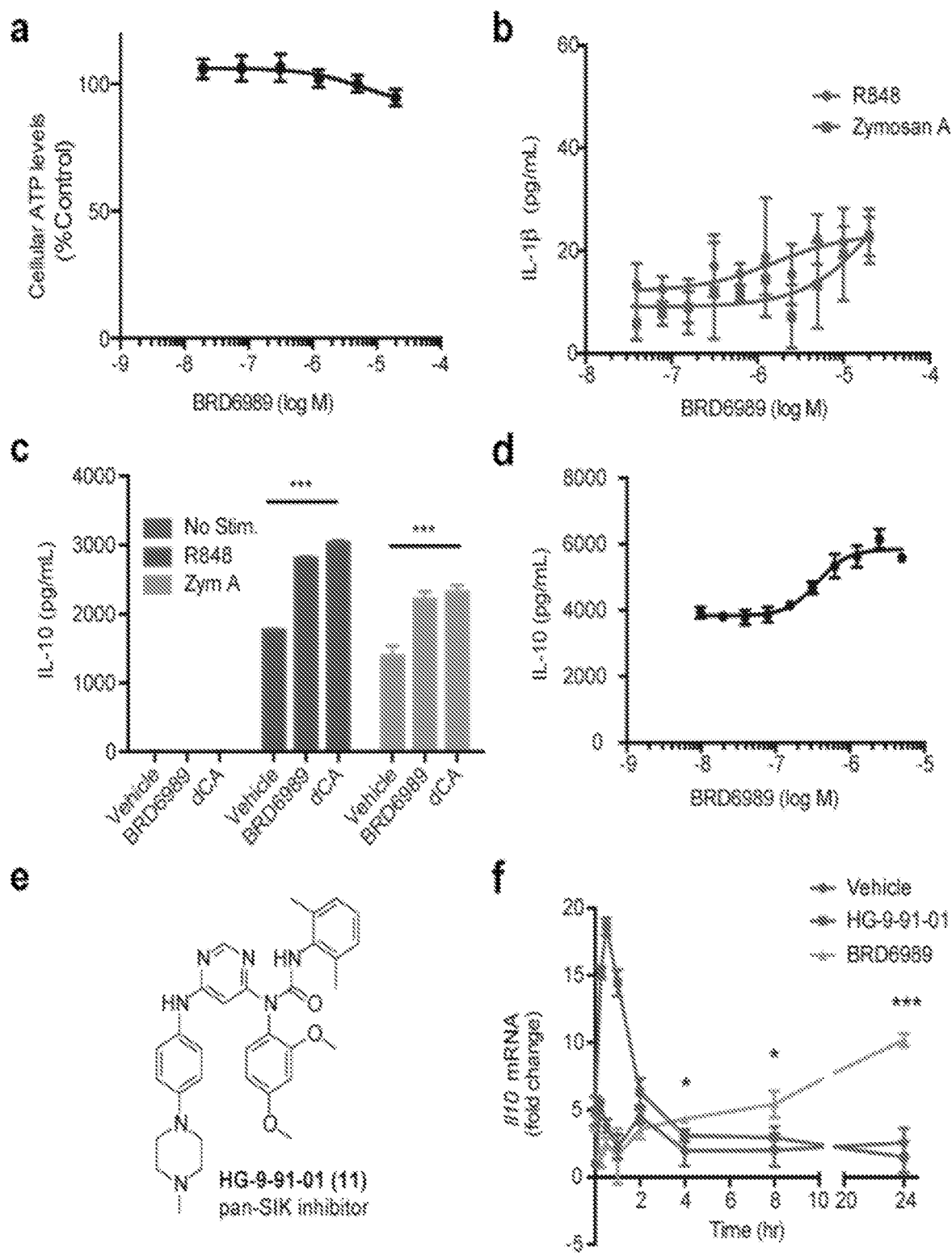
FIG. 5—Cellular activities of the IL-10 hit BRD6989. (a) BRD6989 does not significantly reduce the viability of zymosan A-stimulated BMDCs (each point corresponds to mean±S.D.; n=3 biological replicates from 1 independent experiment). (b) Pre-treatment of BMDCs with BRD6989 minimally elevates IL-1β production induced by stimulation with R848 or Zymosan A (each point corresponds to mean±S.D.; n=3 biological replicates from 1 independent experiment). (c) Pre-treatment of BMDMs with BRD6989 or dCA up-regulates IL-10 production by R848- or Zymosan A-stimulated BMDMs (each bar corresponds to mean±S.D.; n=3 biological replicates for 1 independent experiment). ***, $P<0.001$ using one-way ANOVA with Dunnett's post-test. (d) Effect of BRD6989 on IL-10 production in human DCs stimulated with R848 (each point corresponds to mean±S.D.; n=3 biological replicates from 1 independent experiment using cells derived from 1 donor). (e) Chemical structure of the pan-SIK inhibitor HG-9-91-01. (f) Effect of pre-treating BMDCs with HG-9-91-01 (0.5 μM) or BRD6989 (5 μM) on IL-10 mRNA levels following stimulation with R848 (each point corresponds to mean±S.D.; n=4 biological replicates from 1 independent experiment; *, $P<0.05$; ***, $P<0.001$ using unpaired, two-tailed Student's t test). Data from all panels is representative of at least 2 independent experiments.

The pyridinyl tetrahydroquinoline BRD6989 (10) emerged as a prioritized hit in the screen (FIG. 2a and Table 2). Pre-treatment of BMDCs with BRD6989 for 48 hr prior to stimulation with the yeast cell wall extract Zymosan A for 18 hr increased IL-10 production with an EC50~1 µM (FIG. 2), while only modestly reducing cell viability in these assay conditions (FIG. 5a). In addition, BRD6989 suppressed Zymosan A-induced release of the inflammatory cytokine IL-6, while leaving production of TNFα, IL-12p40 and IL-1β largely unchanged (FIGS. 2b and 5b). BRD6989 induced similar cytokine responses in BMDCs stimulated with the viral RNA mimetic R848, but with a greater fold-increase in IL-10 production (FIGS. 2c and 5b). Along with BMDCs, BRD6989 increased IL-10 production in mouse bone marrow-derived macrophages (BMDMs) activated with Zymosan A or R848 (FIG. 5c). Lastly, BRD6989 up-regulated IL-10 following R848 stimulation in human, monocyte-derived DCs from two independent donors at concentrations consistent with its activity in BMDCs (FIGS. 2d and 5d). Thus, BRD6989 enhances IL-10 production in activated human and murine macrophages and dendritic cells by a mechanism that appears most pronounced following stimulation of toll-like receptors-7 (TLR7) and TLR8 by R848.

tion (Sundberg et al., PNAS 111:12468-12473, 2014), suggesting that inhibition of PI3Ks does not contribute to IL-10 potentiation by BRD6989.

TABLE 2

Chemical Probe Data for BRD-6989

| Category | Parameter | Description |
|---|---|---|
| Compound | Citation | n/a |
| | Name: | BRD-6989 |
| | Chemical descriptors | Smiles: N#Cc1c(N)nc2c(c1c1cccnc1)CC(CC2)C |
| | Chemical compound page | n/a |
| | Entries in chemical databases | Pubchem SID: 7968462 |
| | Availability | Purchased from Vitas M-lab cat# STL241555 |
| | Additional comments | n/a |
| In vitro profiling | Target | CDK8/Cyclin C, CDK19/CyclinC |
| | Potency | Cyclin C/CDK $IC_{50}$ ~0.5 µM and Cyclin C/CDK19 $IC_{50}$ >30 µM |
| | Selectivity | Profiling for binding or inhibition of 405 recombinant kinases identified Cyclin C/CDK8 as the primary kinase target of BRD-6989 |
| | Potential reactivities | None noted |
| | SAR | Pyridine and amino substituents as well as the methyl cyclohexyl core are required for CDK8 binding |
| | Mechanism of inhibition | Not fully characterized |
| | Structure of target-probe complex | Not yet available |
| | Additional comments | n/a |
| Cellular profiling | Validation of cellular target | Dose dependent inhibition of CDK8 dependent phosphorylation of STAT1 S727 phosphorylation. |
| | Validation of cellular specificity | (1) Multiple structural distinct CDK8 inhibitors phenocopy the IL-10 enhancing activity of BRD-6989. (2) Genetic deletion of Cyclin C abrogates the IL-10 enhancing activity of BRD-6989. |
| | Additional comments | n/a |

Analyzing the effects of BRD6989 pre-treatment on IL-10 mRNA levels following R848 stimulation revealed a sustained increase beginning at 4 hours and extending to 24 hours (FIG. 5f). These transcript dynamics contrast with activators of CREB-dependent transcription like the pan-SIK inhibitor HG-9-91-01 (11) (Clark et al., PNAS USA 109:16986-91, 2012), which elevate Il-10 mRNA immediately following microbial stimulation without greatly extending the duration of this response (FIG. 5f). Based on its ability to selectively potentiate IL-10 production by a mechanism that appears temporally distinct from CREB activation, BRD6989 was prioritized for MOA studies.

The Mediator-Associated Kinase CDK8 is a Molecular Target of BRD6989

Figure 6:
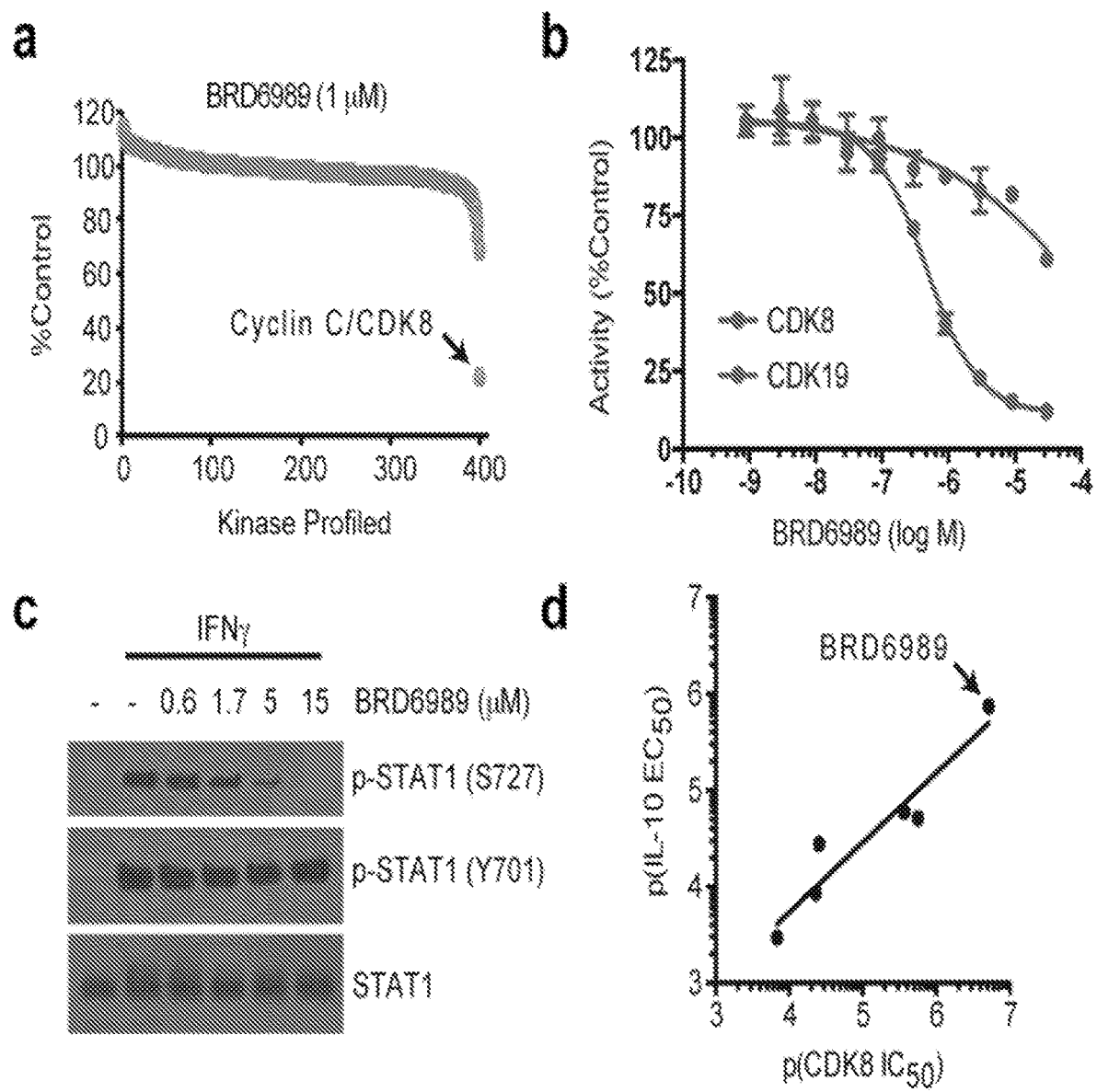
FIG. 6—CDK8 is a molecular target of BRD6989. (a) Kinase profiling identifies Cyclin C/CDK8 as a molecular target of BRD6989 (each point corresponds to the mean of 3 biological replicates from 1 independent experiment). (b) Effect of the indicated concentrations of BRD6989 on the activity of Cyclin C/CDK8 or Cyclin C/CDK19 complexes (each point corresponds to mean±S.D.; n=3 biological replicates from 1 independent experiment for Cyclin C/CDK8 or n=2 biological replicates from 1 independent experiment for Cyclin C/CDK19). (c) BRD6989 suppresses phosphorylation of the STAT1 transactivation domain at S727 in IFNγ-stimulated BMDCs (data is representative of 3 independent experiments). (d) CDK8 binding affinity (IC50) correlates with the potency of IL-10 up-regulation ($EC_{50}$) for BRD6989 and its derivatives ($R2=0.91$) ($IC_{50}$ and $EC_{50}$ data is from 1 independent experiment).
Figure 7:
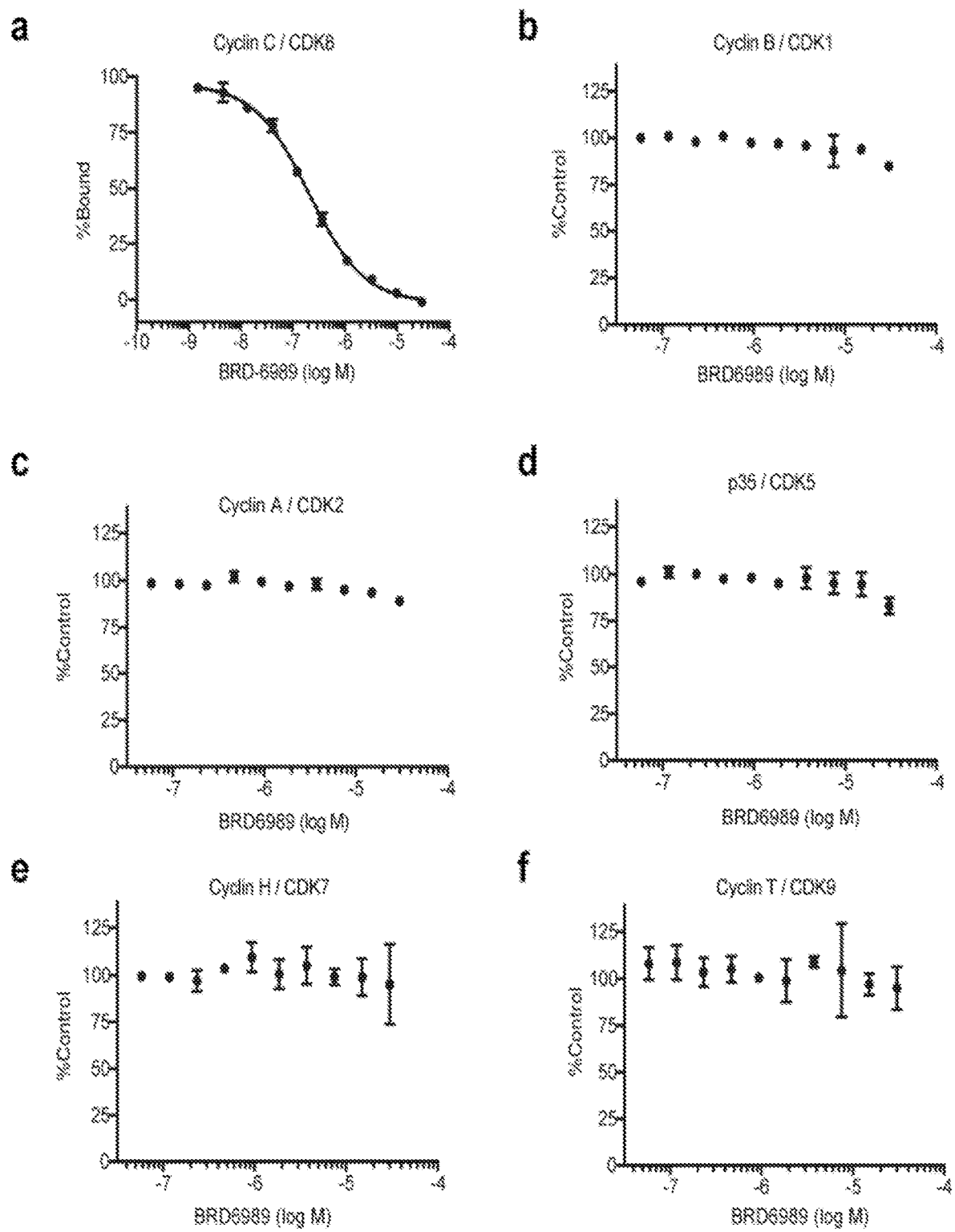
FIG. 7—BRD6989 binds to CDK8, and does not inhibit several other CDKs. (a) Binding of the indicated concentrations of BRD6989 to CDK8/Cyclin C complexes (each point corresponds to mean±S.D.; n=3 biological replicates from 1 independent experiment). (b-f) Effect of the indicated concentrations of BRD6989 on the activity of (b) Cyclin B/CDK1, (c) Cyclin A/CDK2, (d) p35/CDK5, (e) Cyclin H/CDK7, and (f) Cyclin T/CDK9 (each point corresponds to mean±S.D.; n=3 biological replicates from 1 independent experiment).
Figure 8:
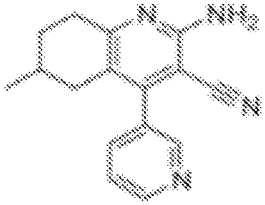
FIG. 8—The potency of CDK8 binding and IL-10 potentiation by BRD6989 and related analogs. CDK8 binding ($IC_{50}$) as well as effects on IL-10 production ($EC_{50}$) by R848-stimulated BMDCs are from 1 independent experiment.
Figure 8:
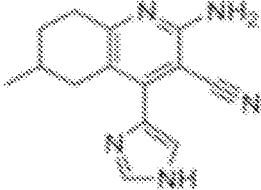
Figure 8:
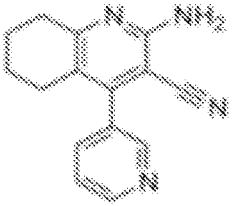
Figure 8:
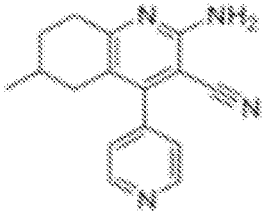
Figure 8:
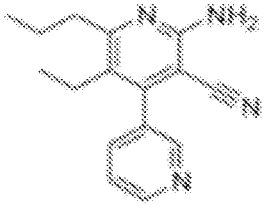
Figure 8:
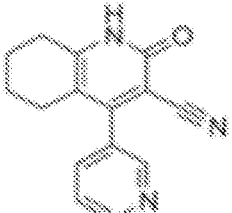

Given that the pyridine core of BRD6989 is a common kinase-binding motif (Xing et al., J Comput Aided Mol Des 28:13-23, 2014), its activity against 414 kinases was profiled using a series of binding and activity assays. It was found that BRD6989 binds a complex of Cyclin C/CDK8, a Mediator-associated kinase not previously linked to IL-10 regulation (Allen et al., Nature Reviews Molecular Cell Biology 16:155-166, 2015), with an IC50~200 nM and remarkable selectivity (FIGS. 6a and 7a). Binding of BRD6989 to CDK8, and its paralog CDK19, was confirmed using an orthogonal kinase-profiling format. In addition to CDK8, both kinase profiling experiments identified phosphatidylinositol-4,5-bisphosphate 3-kinases C2A (PI3KC2A) and PI3KCG as secondary targets of BRD6989 suggesting an overall consistency between the approaches. Of note, PI3K inhibitors with varying isoform specificity screened in this assay system fail to enhance IL-10 produc- In agreement with the kinase profiling results, BRD6989 inhibits the kinase activity of recombinant Cyclin C/CDK8 or Cyclin C/CDK19 complexes with IC50's ~0.5 µM and >30 µM, respectively (FIG. 6b), but not the activity of several CDKs involved in cell cycle regulation (FIG. 7b-f). Furthermore, pre-incubation of BMDCs with BRD6989 inhibited IFNγ-induced phosphorylation of STAT1 at the known CDK8-regulated position S727 (Bancerek et al., Immunity 38:250-262, 2013), but did not affect JAK-mediated phosphorylation of Y701 (FIG. 6c). Preliminary SAR analysis of BRD6989's effects on CDK8 and IL-10 suggest that the pyridine and amino substituents and the methyl cyclohexyl core make critical contacts with CDK8 (FIG. 8). Notably, the potency of CDK8 binding correlates with that of IL-10 induction for these analogs (FIG. 6d), whereas BRD6989 only inhibits CDK19 at concentrations much greater than the EC50 for IL-10 induction. Together, these kinase profiling, binding assay, enzyme inhibition and cell-based data identify the Mediator-associated kinases CDK8, and to a lesser degree CDK19, as molecular targets of BRD6989.

Figure 9:
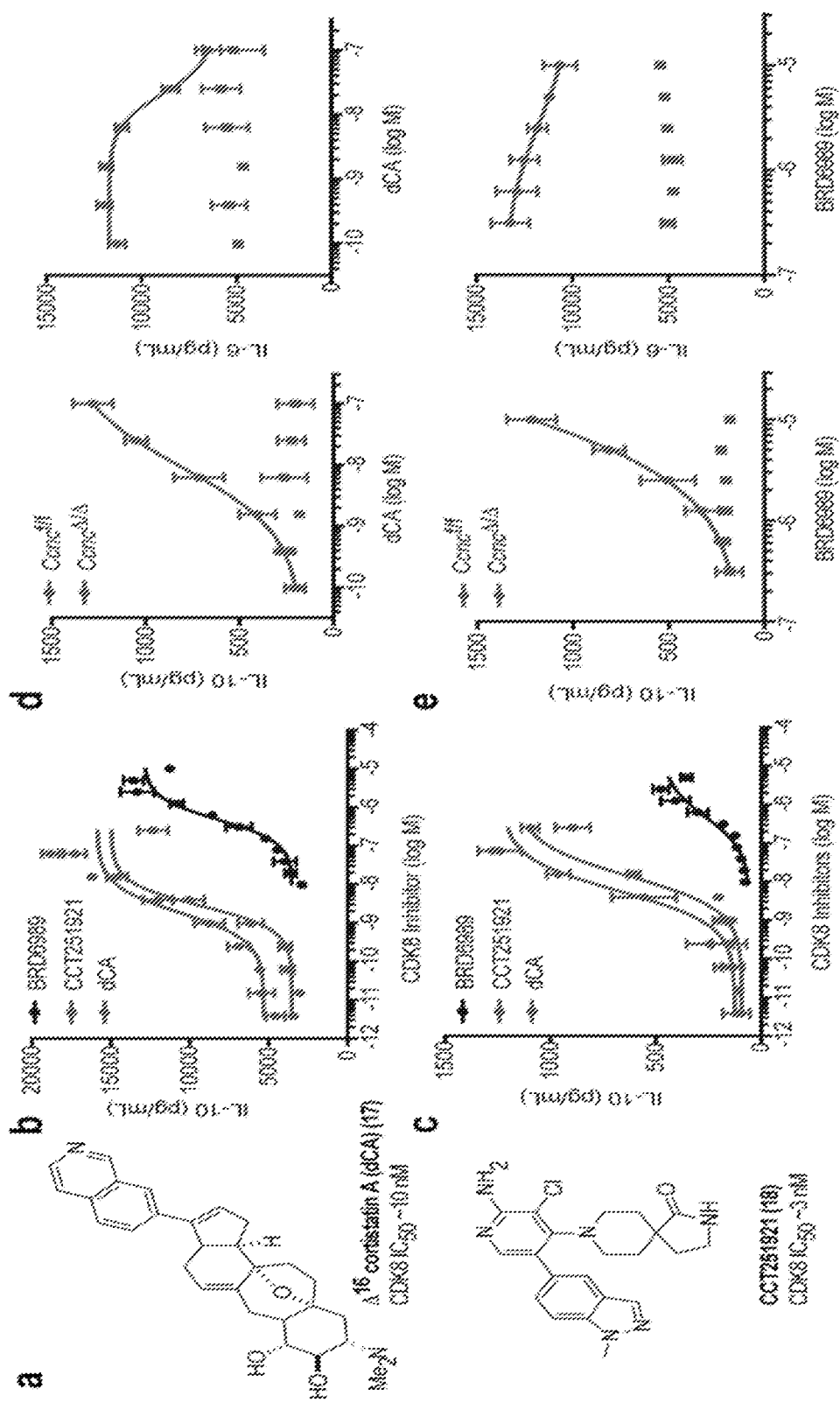
FIG. 9—Pharmacological and genetic data identifying CDK8 as a negative regulator of IL-10 production. (a) Chemical structures of the potent, specific CDK8/19 inhibitors CCT251921 and Δ16-cortistatin A (dCA). (b) CCT251921 and dCA recapitulate the IL-10 enhancing activity of BRD6989 in R848-stimulated BMDCs (each point corresponds to mean±S.D.; n=3 biological replicates from 1 independent experiment). (b) CCT251921 and dCA recapitulate IL-10 potentiation by BRD6989 in human DCs stimulated with R848 (each point corresponds to mean±S.D.; n=3 biological replicates from 1 independent experiment using cells derived from 1 donor). (d,e) Deletion of Cyclin C in BMDCs derived from CcncΔ/Δ mice impairs induction of IL-10 and suppression of IL-6 by (d) dCA or (e) BRD6989 following activation with R848 (each point correspond to mean±S.D.; n=4 biological replicates from 1 independent pair of $Ccnc^{\Delta/\Delta}$ or $Ccnc^{f/f}$ mice). All data is representative of at least 2 independent experiments.
Figure 10:
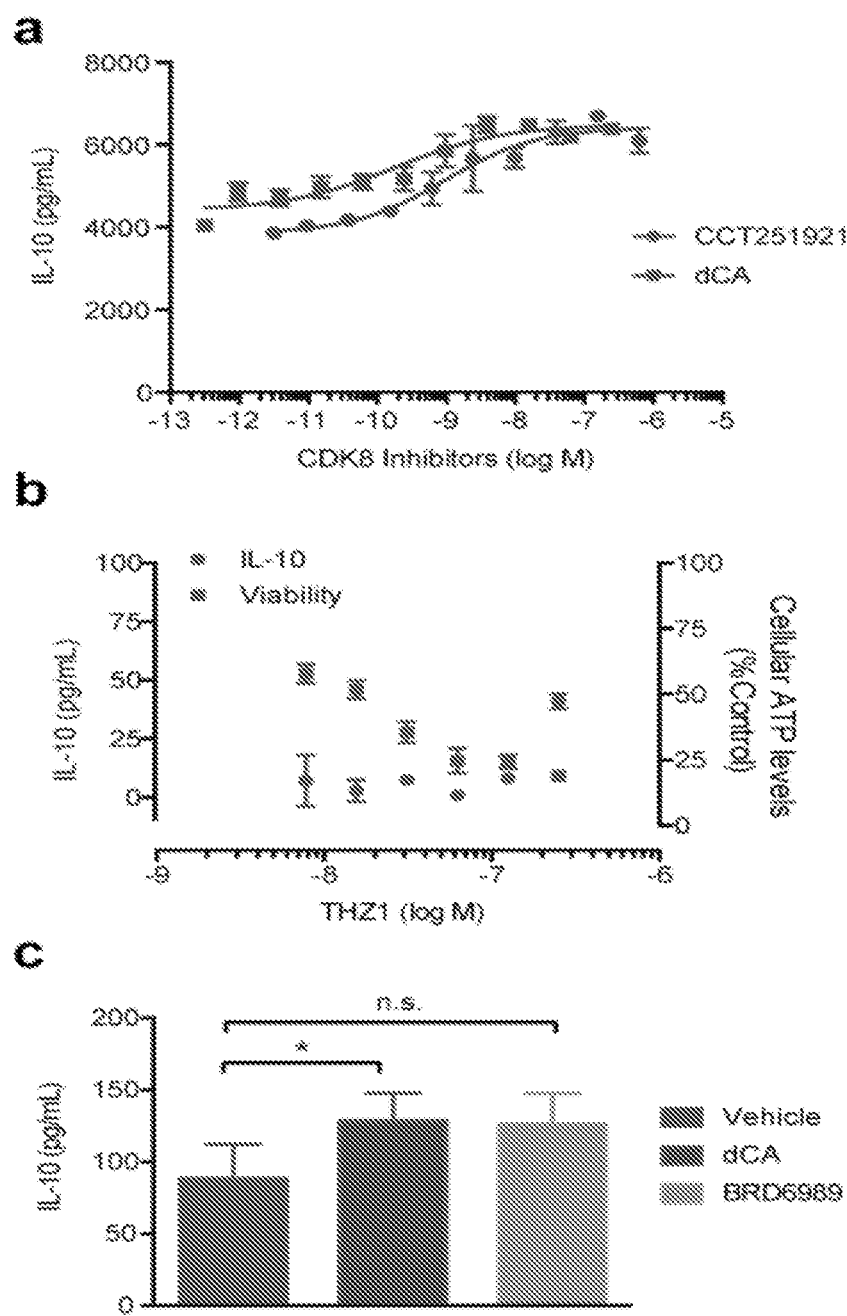
FIG. 10—Cellular activities of CDK8 inhibitors. (a) CCT251921 and dCA recapitulate IL-10 potentiation by BRD6989 in human DCs stimulated with R848 (each point corresponds to mean±S.D.; n=3 biological replicates from 1 independent experiment using cells derived from 1 donor). (b) Effect of CDK7 inhibitor THZ1 on viability and IL-10 production of R848-stimulated BMDCs (each point corresponds to mean±S.D.; n=4 biological replicates from 1 independent experiment). (c) IL-10 levels were quantified in tissue culture media generated during differentiation of naïve, splenic CD4+ T cells into Treg's in the presence of dCA (0.1 μM) or BRD6989 (5 μM) (each point correspond to mean±S.D.; n=3 biological replicates from 1 independent experiment; *, $P<0.05$; n.s., not significant using one-way ANOVA with Dunnett's post-test). Data from all panels is representative of at least 2 independent experiments.

Pharmacological and Genetic Evidence Supports CDK8 as a Regulator of IL-10 Production During Innate Immune Activation Burgeoning interest in Mediator-associated kinases as chemotherapeutic targets has prompted development of several structurally distinct CDK8/19 inhibitors including A-cortistatin A (dCA; 17) (Bancerek et al., Immunity 38:250-262, 2013), an analog of the potent, CDK8/19-selective natural product cortistatin A (Shi et al., J American Chemical Society 133:8014-8027, 2011; Pelish et al., Nature 526:273, 2015) and the recently published highly selective CDK8/19 inhibitor CCT251921 (18) (Mallinger et al., J Medicinal Chemistry 59:1078-1101, 2016) (FIG. 9a). Pre-treatment with these CDK8/19 inhibitors recapitulated the IL-10 potentiating activity of BRD6989 in both BMDCs (FIG. 9b) along with human DCs derived from two independent donors in the context of R848 stimulation (FIGS. 9c and 10a). Significantly, the IL-10 potentiating activity of these three inhibitors occurs as concentrations consistent with their potencies for CDK8/19 inhibition. In contrast, IL-10 production is not enhanced by the CDK7-targeting inhibitor THZ-1 (Kwiatkowski et al., Nature 511:616, 2014) (FIG. 10b), suggesting that this effect does not occur in response to inhibition of other transcriptional regulatory kinases. Lastly, the effect of CDK8 inhibition on IL-10 production may be cell type-specific because neither dCA nor BRD6989 dramatically increased IL-10 production during ex vivo differentiation of Treg's (FIG. 10c). Taken together, these data support CDK8 inhibition as the mechanism driving IL-10 potentiation in response to BRD6989 in activated human and murine DCs.

Figure 11:
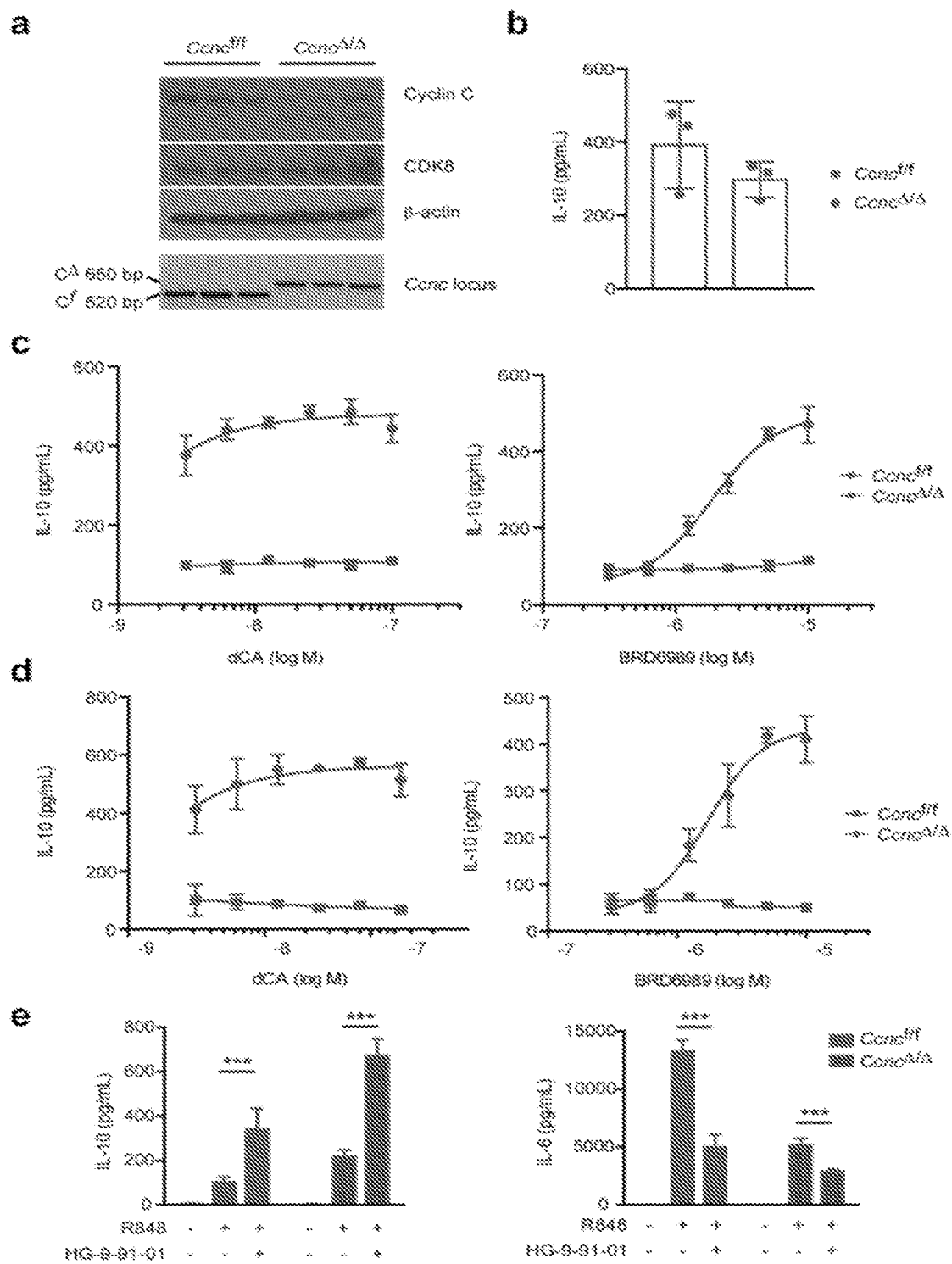
FIG. 11—Upregulation of IL-10 by CDK8 inhibitors requires an intact CDK8/cyclin C complex. (a) Genotyping PCR of genomic DNA and immunoblotting of whole cell lysates confirms recombination of the Ccnc locus and reduction of Cyclin C levels, respectively, in BMDCs derived from $Ccnc^{\Delta/\Delta}$ mice. (b) Reduction of cyclin C levels in BMDCs does not alter basal levels of IL-10 production in response to R848 (each bar represents mean±S.D.; n=3 independent biological replicates from 3 pairs of $Ccnc^{\Delta/\Delta}$ versus $Cncc^{f/f}$ mice). (c,d) Effect of CDK8 inhibition by dCA or BRD6989 on IL-10 production by R848-stimulated BMDCs derived from $Ccnc^{\Delta/\Delta}$ or $Cncc^{f/f}$ mice (each point corresponds to mean±S.D.; n=3 biological replicates for 2 independent pairs of $Ccnc^{\Delta/\Delta}$ versus $Cncc^{f/f}$ mice). (e) (f) Effect of pan-SIK inhibition by HG-9-91-01 (0.5 μM) on production of IL-10 and IL-6 by R848-stimulated BMDCs derived from $Ccnc^{\Delta/\Delta}$ or $Cncc^{f/f}$ mice (each point corresponds to mean±S.D.; n=3 biological replicates for 1 independent pair of $Ccnc^{\Delta/\Delta}$ versus $Cncc^{f/f}$ mice). ***, P<0.001 using unpaired, two-tailed Student's t test.

Next, to determine whether IL-10 potentiation by CDK8 inhibitors requires functional Cyclin C/CDK8 complexes, differentiation was performed of BMDCs from Ccnc$\Delta/\Delta$ mice in which Cyclin C can be specifically disrupted in hematopoietic cells relative to Ccncf/f littermates, which lack the polyinosinic:polycytidylic acid (polyI:C)-responsive Mx1-Cre (Li et al., Nature Cell Biology 16; 1080, 2014) (FIG. 11a). Notably, there was not a significant difference in the levels of IL-10 secreted between Ccnc$\Delta/\Delta$ and Ccncf/f following R848 stimulation (FIG. 11b), suggesting that other regulatory mechanisms can compensate for a sustained loss of CDK8 activity and maintain low basal levels of IL-10 production. However, Ccnc$\Delta/\Delta$ BMDCs failed to upregulate IL-10 in response to dCA or BRD6989, whereas the response remained intact in Ccncf/f BMDCs (FIGS. 9d,e and 11c,d). In addition, Ccnc$\Delta/\Delta$ BMDCs displayed a 50% reduction in IL-6 production relative to Ccncf/f BMDCs and saturating concentrations of dCA or BRD6989 caused no further reduction (FIG. 9d,e). Cyclin C deletion does not appear to inhibit cytokine production non-specifically since it does not affect IL-10 and IL-6 responses induced by pan-SIK inhibition with HG-9-91-01 (FIG. 11e). The impaired response of BMDCs lacking Cyclin C to BRD6989 and dCA are consistent with a model in which CDK8 restrains IL-10 production during activation of wild type myeloid cells.

Figure 12:
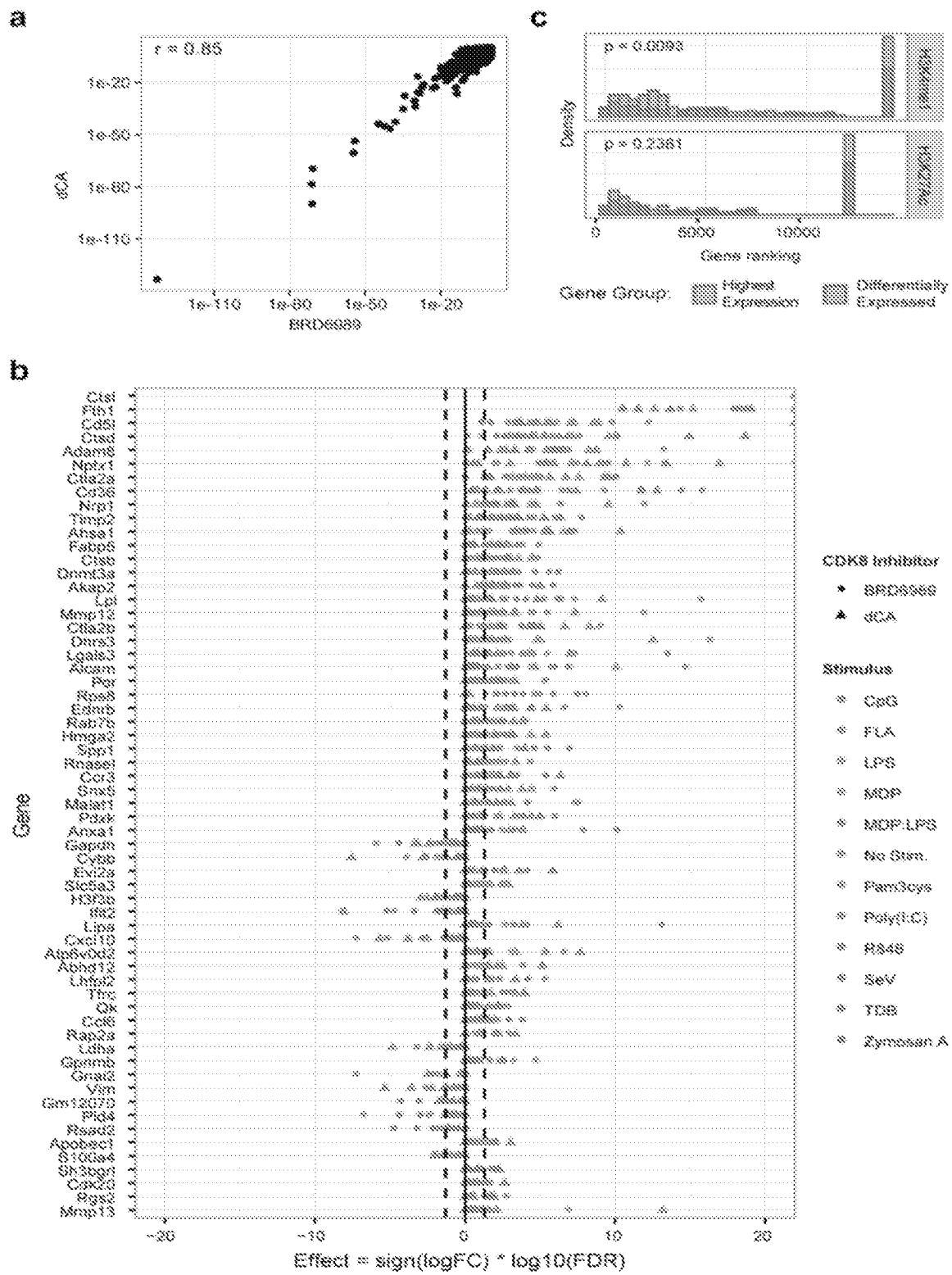
FIG. 12—CDK8 inhibition increases expression of small subset of genes in activated and quiescent macrophages. (a) Changes in gene expression induced by the CDK8 inhibitors dCA and BRD6989 in activated BMDMs are highly correlated. (b) Inhibition of CDK8 with the structurally distinct inhibitor dCA and BRD6989 up-regulates expression of a small subset of genes in both quiescent BMDMs and following stimulation with a variety of microbial products. For (a,b), gene expression data is integrated from time points from 15 min 4 hr from 1 independent experiment; dashed lines correspond to FDR<0.05 as corrected by Benjamin-Hochberg testing. (c) Enrichment of mono-methylated Lys-4 on histone 3 (H3K4me1) and acetylated Lys-27 on histone 3 (H3K27ac) among the subset of genes induced by CDK8 inhibition relative to all highly expressed genes. CpG, synthetic CpG-containing oligonucleotide; FLA, flagellin; LPS, lipopolysaccharide; MDP, muramyldipeptide; Pam3cys, synthetic triacylated lipoprotein; Poly(I:C), polyinosinic-polycytidylic acid; SeV, Sendai virus; TDB, trehalose-6,6-dibehenate.

Pharmacological Inhibition of CDK8 Induces Gene-Specific Transcriptional Responses in Activated Myeloid Cells To define systematically the role of CDK8 during innate immune activation, the transcriptional responses elicited by dCA or BRD6989 following stimulation of BMDMs were profiled with a panel of 10 microbial ligands or Sendai virus for time points from 15 min to 4 hours. BMDMs were chosen for these experiments because, like human and mouse DCs, they upregulate IL-10 in response to CDK8 inhibition (FIG. 5c), and they have been previously studied using the multiplexed pathway reporter assay described below (O'Connell, et al., Cell Syst 2:323-34, 2016). In this experiment, the transcriptional responses elicited by BRD6989 and dCA were highly correlated (FIG. 12a), again supporting CDK8 as a principle cellular target of BRD6989. For instance, both CDK8 inhibitors reduced expression of the interferon-inducible genes Ifit2, Cxcl10 and Rsad2 (FIG. 12b). Given that CDK8-dependent phosphorylation of STAT1 at Ser727 is required for expression of many IFNγ-inducible genes (Bancerek et al., Immunity 38:250-262, 2013), these suppressive effects suggest that CDK8 inhibition may limit autocrine interferon signaling following microbial stimulation.

In addition to suppressing interferon-inducible genes, BRD6989 and dCA increased abundance of a similar, small subset of transcripts in both quiescent and activated BMDMs (FIG. 12b). Consistent with the effects of CDK8 inhibition on cytokine responses in activated myeloid cells, the induced genes include chemokines, metallopeptidases and regulators of cellular second messengers linked to inflammatory responses and migration of innate immune cells (P=0.0255 and P=1.52×10-5, respectively). In the context of acute myeloid leukemia (AML), CDK8 inhibition preferentially induces genes near 'super enhancers' (SEs) defined by dense binding of the Mediator complex and transcription factors along with accumulation of histone modifications associated with active transcription (Pelish et al., Nature 526:273, 2015). Acknowledging the limitations in comparing datasets from different myeloid cell types, genes upregulated in BRD6989- or dCA-treated BMDMs were queried for the presence of histone modifications linked to active transcription previously identified in lipopolysaccharide (LPS)-stimulated BMDCs (Garber et al., Mol Cell 47:810-22, 2012). In this analysis, mono-methylated Lys-4 on histone 3 (H3K4me1), a mark associated with poised enhancers (Witte et al., Trends Immunol 36:519-26, 2015; Shlyueva et al., Nature Reviews Genetics 15:272-286, 2014), is enriched (P=0.0093) near genes induced by CDK8 inhibition relative to all highly expressed genes (FIG. 12c). Although a similar trend was detected towards enrichment of histone 3 Lys27 acetylation (H3K27ac), a modification associated with active enhancers (Witte et al., Trends Immunol 36:519-26, 2015; Shlyueva et al., Nature Reviews Genetics 15:272-286, 2014), near genes induced by CDK8 inhibition, this association did not achieve statistical significance (FIG. 12c). These data indicate that CDK8 primarily represses a small set of genes in quiescent or activated myeloid cells, although the link between CDK8-regulated genes and histone modifications associated with active transcription appears less well correlated in this context.

Figure 13:
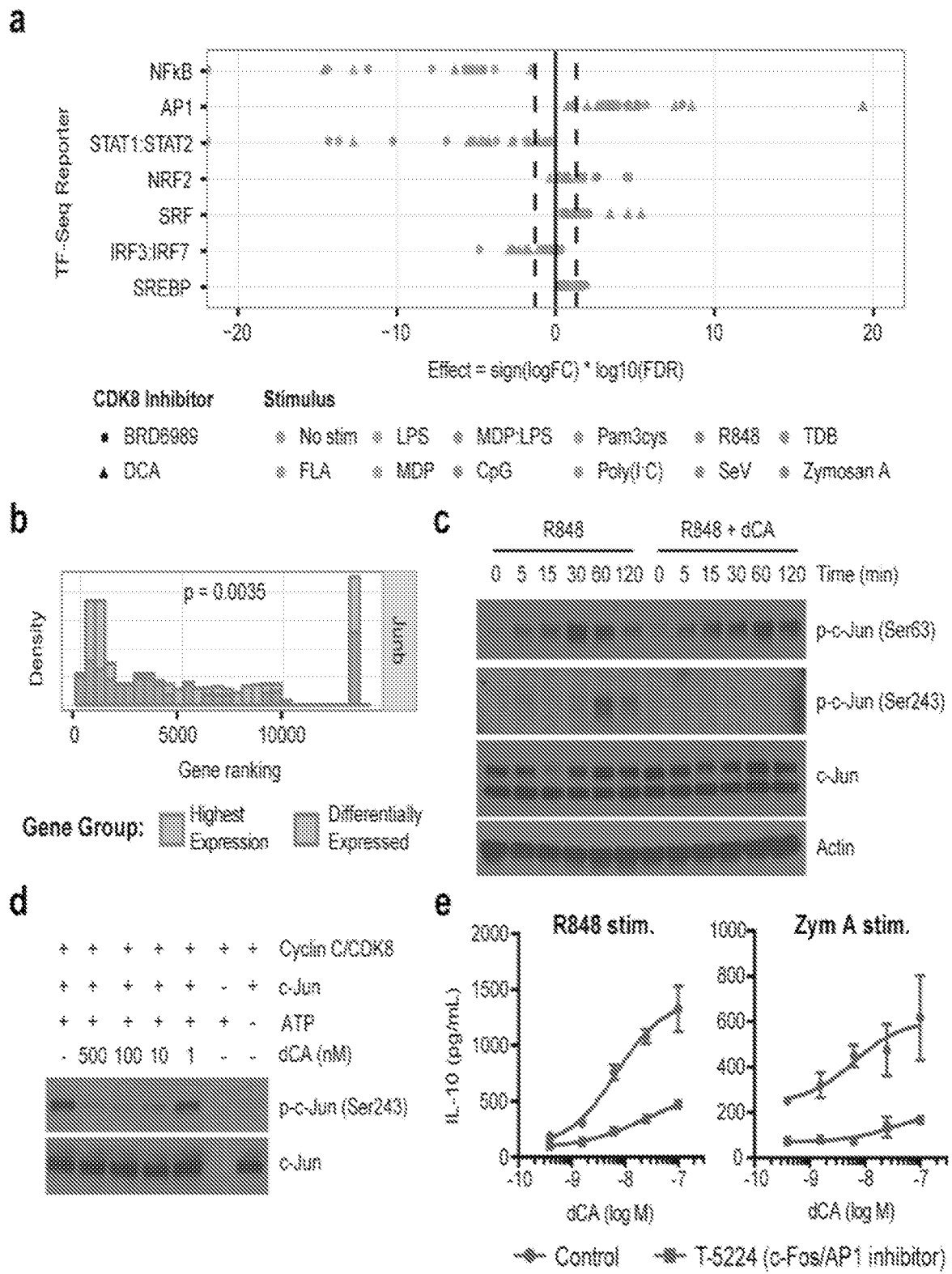
FIG. 13—Modulation of c-Jun/AP-1 links CDK8 inhibition to enhanced IL-10 production. (a) CDK8 responsive signaling pathways in activated BMDMs as identified by the highly parallel reporter gene assay TF-Seq. Reporter data is integrated for time points between 15 min 4 hr from 1 independent experiment. Dashed lines correspond to FDR<0.05 as corrected by Benjamin-Hochberg testing. (b) Relative to all highly expressed genes, JunB binding sites are enriched among the subset of genes induced by CDK8 inhibition (see Online Methods). (c) Pre-treatment with dCA (100 nM; 18 hr) suppresses phosphorylation of c-Jun on Ser243 in BMDCs activated with R848 (2 µg/mL) for the indicated times. Data is representative of 2 independent experiments. (d) The indicated concentrations of dCA suppress phosphorylation of recombinant c-Jun at Ser243 by recombinant Cyclin C/CDK8 in an in vitro kinase reaction. Data is representative of 2 independent experiments. (e) Co-treatment of BMDCs with the c-Fos/AP-1 inhibitor T-5224 (100 µM) suppresses the IL-10 enhancing activity of dCA in BMDCs stimulated with R848 or Zymosan A (each point correspond to mean±S.D.; n=3 biological replicates from 1 independent experiment; data is representative of 3 independent experiments). CpG, synthetic CpG-containing oligonucleotide; FLA, flagellin A; LPS, lipopolysaccharide; MDP, muramyldipeptide; Pam3cys, synthetic triacylated lipoprotein; poly(I:C), polyinosinic-polycytidylic acid; SeV, Sendai virus; TDB, trehalose-6,6-dibehenate.
Figure 14:
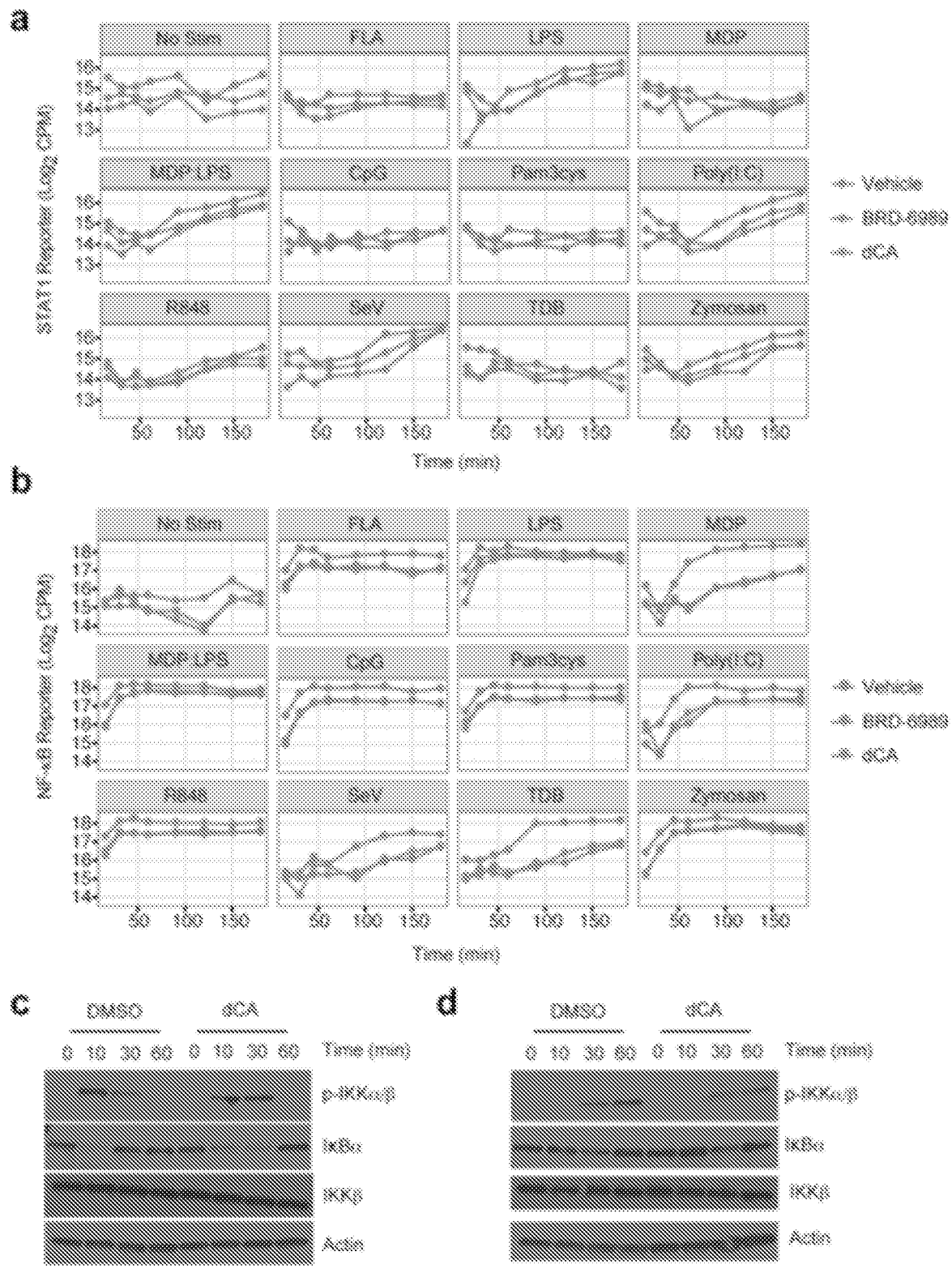
FIG. 14—CDK8 inhibition suppresses STAT1 and NF-κB activity during innate immune activation. Time course of (a) STAT1 and (b) NF-κB reporter activity in BMDMs pre-treated with dCA (0.1 µM) or BRD6989 (5 µM) prior to stimulation with the indicated viruses or microbial ligands. TF-Seq reporter data is derived from 1 independent experiment. (c,d) Pre-treatment with dCA (0.1 µM) does not suppress upstream signaling events leading to NF-κB activation in BMDCs stimulated with (c) LPS or (d) R848 for the indicated time points. Immunoblotting data is representative to 2 independent experiments. CpG, synthetic CpG-containing oligonucleotide; FLA, flagellin; LPS, lipopolysaccharide; MDP, muramyldipeptide; Pam3cys, synthetic triacylated lipoprotein; Poly(I:C), polyinosinic-polycytidylic acid; SeV, Sendai virus; TDB, trehalose-6,6-dibehenate.

CDK8 Inhibition Upregulates IL-10 by a Mechanism that Involves Suppressing Inhibitory Phosphorylation of c-Jun and Enhancing AP-1 Activity To identify CDK8-responsive signaling pathways, an integrative genomics approach termed transcription factor sequencing (TF-Seq) was applied, in which consensus transcription factor binding sites drive expression of 58 reporter constructs bearing unique sequence tags (O'Connell et al., Cell Syst 2:323-34, 2016). Consistent with the established role of CDK8 in STAT1 activation (Bancerek et al., Immunity 38:250-262, 2013), both BRD6989 and dCA suppressed induction of STAT1:STAT2 activity 2 hours after stimulation of BMDMs (FIGS. 13a and 14a). Also similar to previous studies of CDK8 function in other contexts including RPMI8226 myeloma cells activated by TLR9 stimulation (Porter et al., PNAS 109:13799-804, 2012; Poss et al. Cell Rep 15:436-50, 2016; Yamamoto et al., Genes Cells 2017), pre-treatment with dCA or BRD6989 suppressed NF-κB activation to a varying degree for all stimuli tested (FIGS. 13a and 14b). Because dCA pre-treatment does not perturb upstream signaling events linking sensing of LPS or R848 to NF-κB activation (FIG. 14c,d), it appears that inhibiting CDK8 may suppress the ability of nuclear NF-κB to activate transcription.

Figure 15:
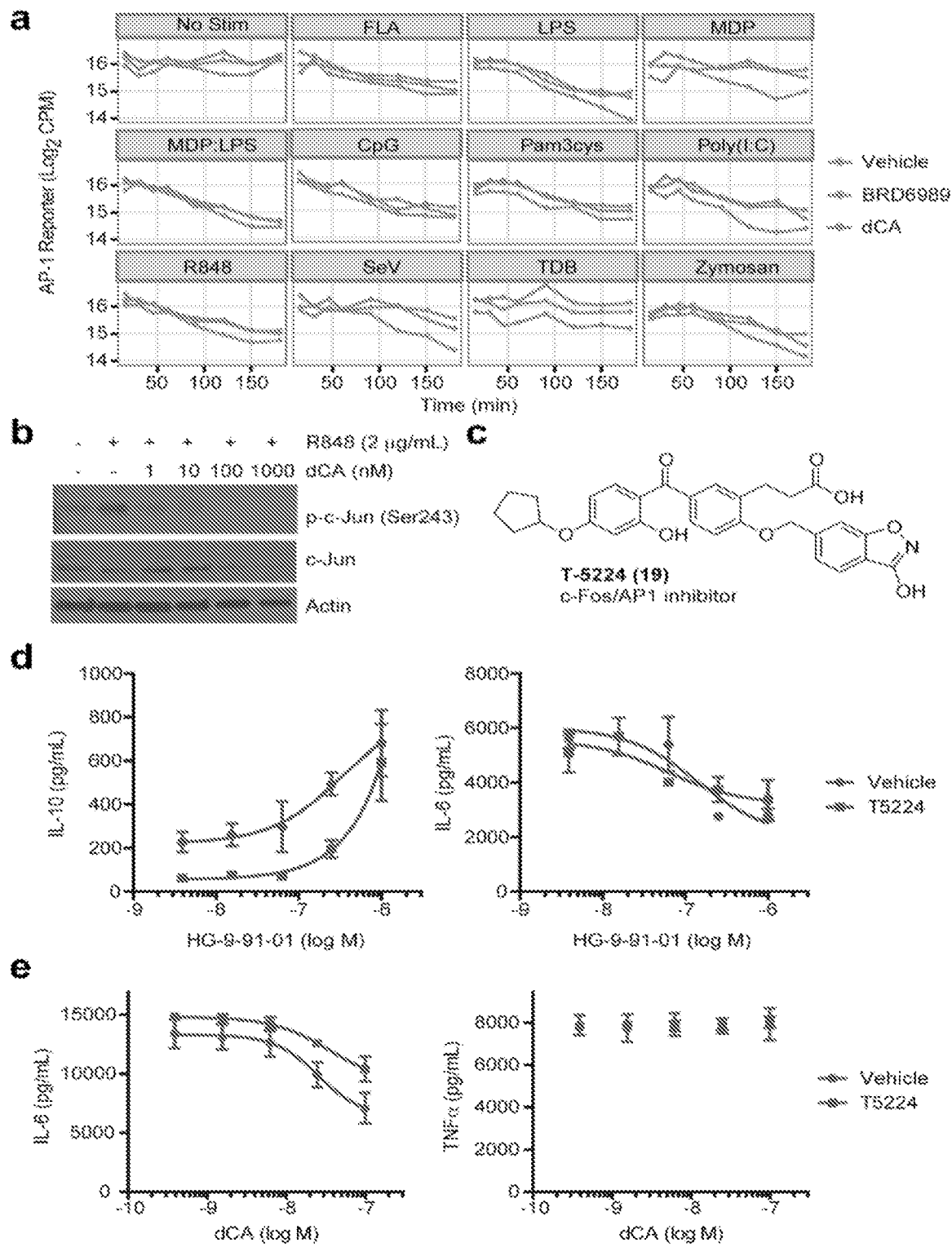
FIG. 15—CDK8 inhibition enhances AP-1 activity during innate immune activation. (a) Time course of AP-1 reporter activity in BMDMs pre-treated with dCA (0.1 µM) or BRD6989 (5 µM) prior to stimulation with the indicated viruses or microbial ligands for the indicated time points (each point corresponds to TF-Seq reporter data derived from 1 independent experiment). (b) Pre-treatment of BMDCs with the indicated concentrations of dCA for 18 hr suppresses R848-induced phosphorylation of c-Jun on Ser243. Data is from 1 independent experiment. (c) Chemical structure of the c-Fos/AP-1 inhibitor T-5224. (c) Co-incubation of BMDCs with T-5224 (100 µM) and the indicated concentration of the pan-SIK inhibitor HG-9-91-01 does not affect up-regulation of IL-10 or suppression of IL-6 in Zymosan A-stimulated BMDCs (each data point corresponds to mean±S.D.; n=3 biological replicates for 1 independent experiment). (d) Co-incubation of BMDCs with T-5224 (100 µM) and the indicated concentration of the dCA does not affect production of IL-6 or TNFα in R848-stimulated BMDCs (each data point corresponds to mean±S.D.; n=3 biological replicates for 1 independent experiment). Data in panels (c,d) are representative of 2 independent experiments. CpG, synthetic CpG-containing oligonucleotide; FLA, flagellin; LPS, lipopolysaccharide; MDP, muramyldipeptide; Pam3cys, synthetic triacylated lipoprotein; Poly(I:C), polyinosinic-polycytidylic acid; SeV, Sendai virus; TDB, trehalose-6,6-dibehenate.

TF-seq also indicates that CDK8 inhibition increases activator protein 1 (AP-1) activity in BMDMs (FIGS. 13a and 15a). In support of this observation, binding sites for the AP-1 subunit JunB are enriched among genes up-regulated following CDK8 inhibition relative to all highly expressed genes (FIG. 13b). Given that c-Jun's ability to activate transcription is tightly regulated by phosphorylation, it was determined whether CDK8 inhibition affects c-Jun phosphorylation in activated BMDCs. It was found that pre-treatment with dCA only moderately delayed the activating phosphorylation of c-Jun on Ser63, which is rapidly induced by R848 stimulation and peaks after 30 minutes (FIG. 13c). In contrast, inhibiting CDK8 with dCA dramatically reduced phosphorylation of Ser243, a suppressive mark shown to destabilize c-Jun and interfere with its ability to bind DNA (Lin et al., *Cell* 70:777-89, 1992; Huang et al., *Oncogene* 27:2422-9, 2008; Taira et al., *J Clin Invest* 122:859-72, 2012), which is first observed 60 minutes after R848 stimulation (FIG. 13c). Significantly, dCA induces concentration-dependent suppression of c-Jun Ser243 phosphorylation in both R848-stimulated BMDCs (FIG. 15b), and in an in vitro kinase reaction with recombinant Cyclin C/CDK8 and c-Jun (FIG. 13d). Together, these data suggest that c-Jun Ser243 is a direct CDK8 substrate that regulates AP-1 activity in activated myeloid cells.

Given the presence of an AP1 consensus motif in IL-10 and evidence that potentiation of MAP kinase signaling can increase IL-10 production (Saraiva et al., *Nat Rev Immunol* 10:170-81, 2010; Wang et al., *Nat Commun* 5:3479, 2014; Na et al., *Science Signaling* 8:2015), it was hypothesized that increased AP-1 activity resulting from reduced c-Jun Ser243 phosphorylation may mediate activation of IL-10 following CDK8 inhibition. Supporting this, it was found that co-treatment of BMDCs with dCA and T-5224 (19), a small-molecule inhibitor of AP-1 reported to bind c-Fos and inhibit its dimerization with c-Jun (Aikawa et al., *Nature Biotechnology* 26:817-823, 2008) (FIG. 15c), suppressed IL-10 production following stimulation with R848 or Zymosan A (FIG. 13e). Importantly, T-5224 co-treatment did not affect the increase in IL-10 production resulting from potentiation of CREB signaling by pan-SIK inhibition with HG-9-91-01, or suppress R848-induced inflammatory cytokine production (FIG. 15d,e). These results suggest that CDK8 inhibition upregulates IL-10 production by a c-Jun/AP-1-dependent mechanism that is distinct from cAMP/CREB signaling.

Discussion

Using unbiased phenotypic screening and MoA studies, this study identified the Mediator-associated kinase CDK8, and likely CDK19, as regulators of IL-10 production, a mechanism that might be harnessed to enhance anti-inflammatory functions of innate immune cells. The initial screen uncovered three new structural classes of small molecules that enhance IL-10 production, including a probe found to bind to CDK8 through kinase profiling (BRD6989). The growing interest in Mediator-associated kinases as therapeutic targets in cancer has spurred development of several chemically distinct CDK8/19 inhibitors such as the potent, dual CDK8/19 inhibitor CCT251921 (Mallinger et al., *J Medicinal Chemistry* 59:1078-1101, 2016), which shares pyridinyl tetrahydroquinoline core with BRD6989, and a close analog of the natural product cortistatin A (dCA) (Shi et al., *J American Chemical Society* 133:8014-8027, 2011; Poss et al., *Cell Rep* 15:436-50, 2016). Though not as potent as these inhibitors, BRD6989 appears unique in its ability to differentially inhibit CDK8 relative to its paralog CDK19, suggesting it may inform further development of CDK8-specific inhibitors. Importantly, it was found that both CCT251921 and dCA, like BRD6989, promote IL-10 production in R848-stimulated DCs in a manner that depends on an intact Cyclin C/CDK8 complex. Together, these data identify CDK8 as a druggable regulator of IL-10 production in activated myeloid cells.

Relative to CDK7 and CDK9, which broadly affect transcriptional initiation by activating phosphorylation of the C-terminal domain of RNAP polymerase II (Kwiatkowski et al., *Nature* 511:616, 2014; Lim et al., *Development* 140:3079-3093, 2013), CDK8's function appears to be more context-dependent, having been linked to specific effects on interferon, TGFβ, Wnt and Notch signaling (Allen et al., *Nature Reviews Molecular Cell Biology* 16:155-166, 2015). For example, phosphorylation of the transactivation domain of STAT1 by CDK8 is required for expression of many interferon-inducible genes (Bancerek et al., *Immunity* 38:250-262, 2013), and inhibiting CDK8 in AML lines with cortistatin A specifically elevates expression of SE-associated genes (Pelish et al., *Nature* 526:273, 2015). Similarly, transcriptional profiling data in BRD6989- or dCA-treated BMDMs suggests that CDK8's kinase function primarily restrains expression of a limited number of genes in myeloid cells. In contrast, preliminary analysis suggested that genes regulated by CDK8 in myeloid cells are less correlated with regions of active transcription (i.e., SE-associated).

Measuring the response to CDK8 inhibition using a multiplex pathway reporter assay (TF-Seq) provided insights into CDK8-sensitive signaling pathways in activated myeloid cells. Consistent with previous studies (Bancerek et al., *Immunity* 38:250-262, 2013), it was observed that CDK8 inhibition reduced activation of STAT1:STAT2 and triggered a corresponding decrease in expression of several interferon-inducible genes. Decreased NF-κB activity was also detected to varying degrees with different microbial stimuli, but which appears to be insufficient in magnitude to suppress expression of NF-κB targets on a genome-wide scale. This intermediate suppressive effect may explain why CDK8 inhibition does not block expression of Il-10, itself an NF-κB target gene (Yamamoto et al., *Genes Cells*, 2017; Saraiva et al., *J Immunol* 175:1041-6, 2005). The data with dCA and BRD6989 contrasts with the recent identification of an essential role for CDK8/19 in NF-κB-dependent Il10 expression following TLR9 stimulation of a B cell-derived myeloma cell line (Yamamoto et al., *Genes Cells*, 2017). While differences in cell type and microbial stimuli may alter the degree to which NF-κB activation depends on CDK8/19, contrasting effects of depleting CDK8/19 by RNA interference versus specifically inhibiting their kinase activity with small molecules may also play a role.

CDK8 inhibition also increased AP-1 reporter activity in the TF-Seq assay for nearly all microbial stimuli tested, and, binding sites for the A-P1 subunit JunB are enriched near genes upregulated in response to CDK8 inhibitors. Enhanced AP-1 activity appears to be important for potentiation of IL-10 following CDK8 inhibition as the Fos-targeting inhibitor T-5224 suppresses this response. In contrast, disrupting AP-1 activity does not impair the ability of BMDCs to increase IL-10 production through a parallel, CREB-dependent pathway triggered by the pan-SIK inhibitor HG-9-91-01. Reduced phosphorylation of the negative regulatory site Ser243 on c-Jun may be central to the mechanism linking CDK8 inhibition to enhanced AP-1 transcriptional activity and IL-10 production in myeloid cells. Of note, CDK8 appears to directly phosphorylate Ser243 in a cell-free biochemical assay in a dCA-dependent manner. The data identifying CDK8 as a negative regulator of c-Jun/AP-1 in activated myeloid cells contrasts with the role for CDK8 in promoting AP-1 activity during serum stimulation of prostate cancer cells (Donner et al., Nat Struct Mol Biol 17:194-201, 2010). As such, while CDK8 appears to regulate c-Jun Ser243 phosphorylation following microbial stimulation of post-mitotic BMDCs, other kinases targeting this site [e.g., casein kinase-2 and Dyrk2 (Lin et al., Cell 70:777-89, 1992; Taira et al., J Clin Invest 122:859-72, 2012)] may play this role in cycling cancer cells.

The present data identify the CDK8/c-Jun module as a regulator of IL-10 production that is distinct from previously described pathways like cAMP/CREB signaling. It remains to be determined whether using CDK8 inhibitors to upregulate IL-10 will be an efficacious and tolerated treatment for inflammatory disorders. The clinical observations that targeted delivery of IL-10 to inflamed tissues can suppress inflammation suggest that recapitulating this strategy with small molecules may hold promise (Braat et al., Clin Gastroenterol Hepatol 4:754-9, 2006; Galeazzi et al., Isr Med Assoc J 16:666, 2014). Notably, CDK8 selectively upregulates IL-10 production by activated myeloid cells suggesting its immunomodulatory activity could be localized to sites of inflammation circumventing dose-limiting toxicities associated with systemic delivery of IL-10 (Schreiber et al., Gastroenterology 119:1461-72, 2000; Marlow et al., World J Gastroenterol 19:3931-41, 2013). In addition, given that increased IL-10 expression and other mechanisms that suppress anti-tumor immune responses have well-established links to tumor progression and resistance to chemotherapy (Itakura et al., Mod Pathol 24:801-9, 2011; Pyonteck et al., Nat Med 19:1264-72, 2013; Wang et al., Eur J Oral Sci 122:202-9, 2014), the anti-inflammatory effects of CDK8/19 inhibition described here warrant consideration in the context of targeting these kinases in cancer.

Given that CDK8/19 are fundamental regulators of transcription in numerous cell types, it is not surprising that small-molecule inhibitors of these Mediator-associated kinases are poorly tolerated in vivo at doses that achieve the sustained target occupancy required for anti-tumor activity (Clarke et al., Elife 5, 2016). Although these toxicities may preclude therapeutic targeting of CDK8/19, it is possible that the anti-inflammatory consequences of CDK8/19 inhibition can be achieved in vivo using less aggressive dosing regimens. The data suggest that inhibiting CDK8/19 affects a limited number of pathways in myeloid cells including several targeted by clinically approved inhibitors of Janus kinases and the proteasome, respectively (Yamaoka, Curr Opin Chem Biol 32:29-33, 2016; Miller et al., Biochemical Pharmacology 79:1272-1280, (2010). Thorough investigation of potential toxicities associated with immunomodulatory doses of CDK8/19 inhibitors in vivo will be a critical next step for evaluating the potential of developing therapeutics targeting these Mediator-associated kinases for treatment of inflammatory disorders.

Example 2

Figure 16:
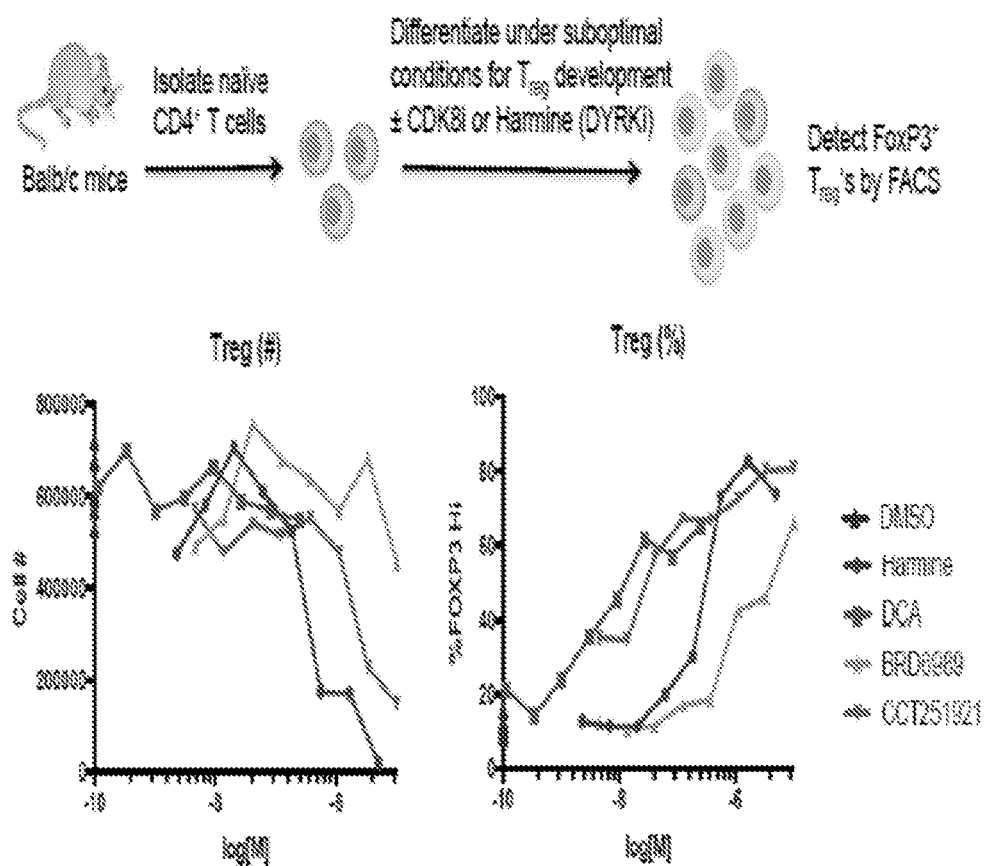
FIG. 16—CDK8 inhibition promotes ex vivo differentiation of FoxP3+ Treg cells. Numbers of viable, CD4+ T cells were quantified in cultures of naive splenic CD4+ T cells differentiated toward the Treg lineage for 4 d in the presence of different CDK8 inhibitors (dCA, BRD6989, CCT251921) at the indicated concentrations. The DYRK1 inhibitor harmine was used as a positive control. Assay was performed as described in eLife 2015; 4:e05920.
Figure 17:
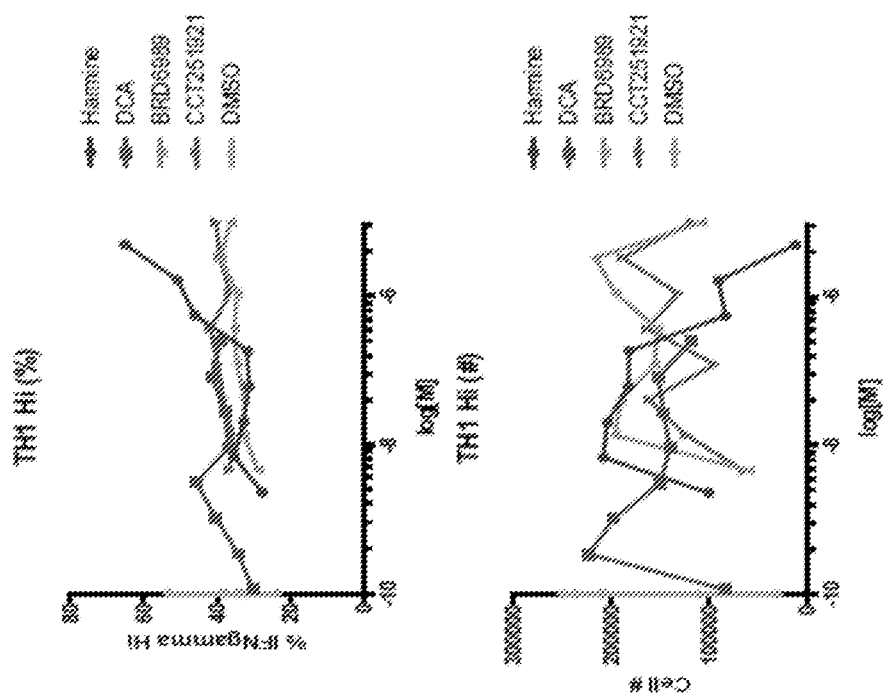
FIG. 17—CDK8 inhibition shows no impact on Th1 differentiation, indicating that the effect is limited to the anti-inflammatory $T_{reg}$ lineage. Compounds were tested under both suboptimal (TH1 lo) and optimal (TH1 hi) conditions for TH1 differentiation. Assay was performed as described in eLife 2015; 4:e05920.
Figure 17:
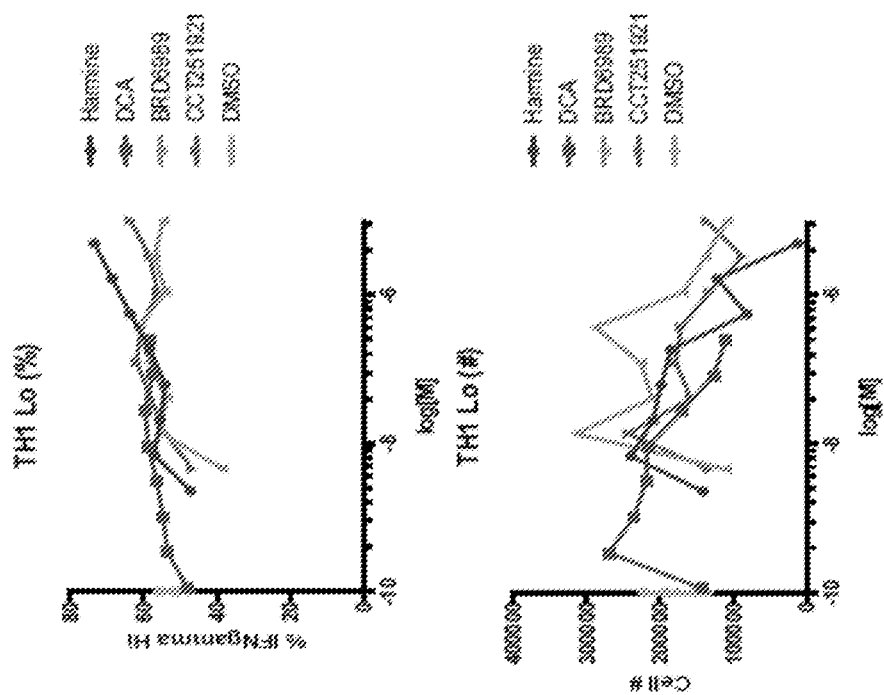
Figure 18:
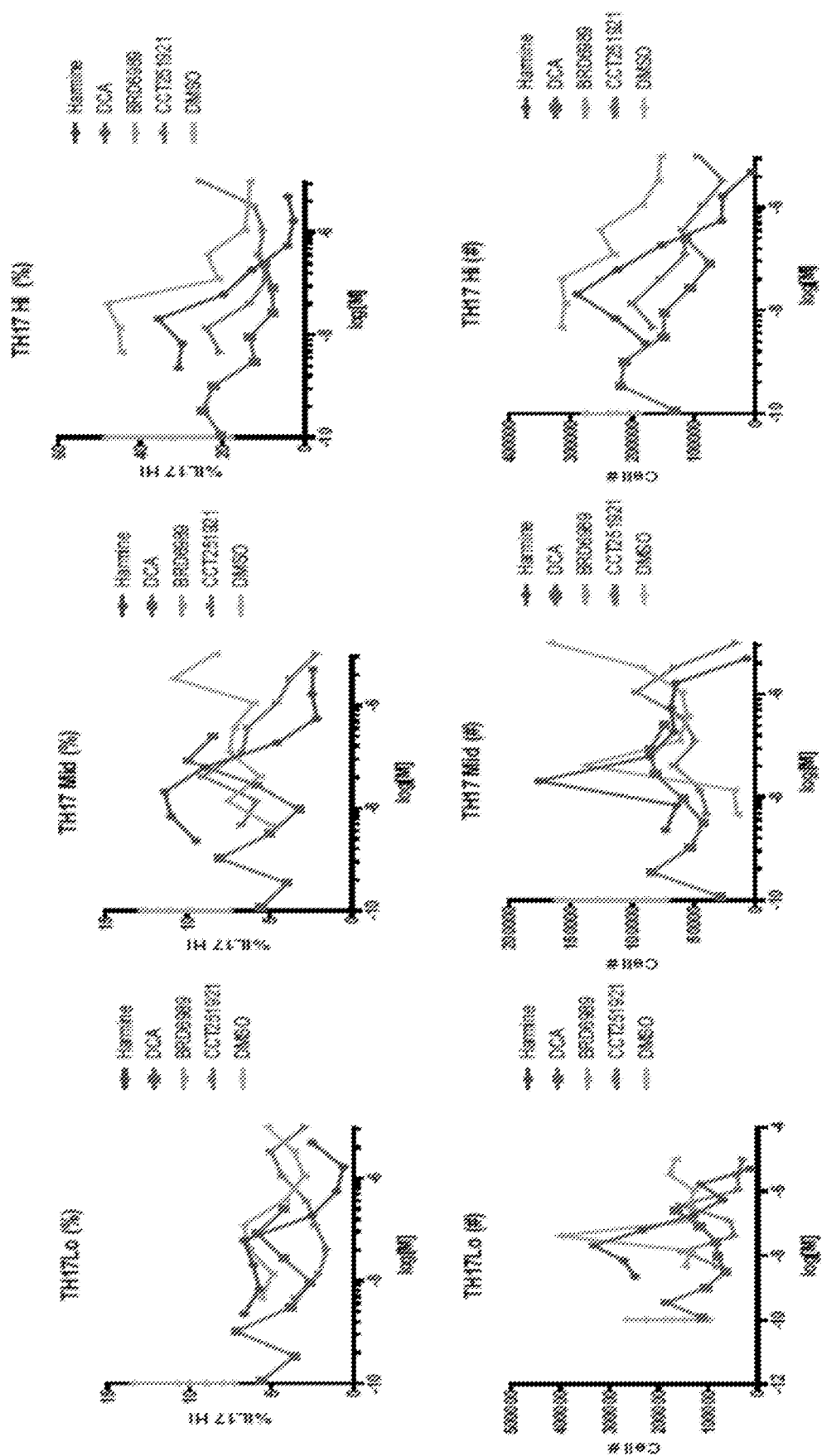
FIG. 18—CDK8 inhibition shows no impact on Th17 differentiation, indicating that the effect limited to the anti-inflammatory $T_{reg}$ lineage. Compounds were tested under both suboptimal (TH17 lo), intermediate (TH17 mid), and optimal (TH17 hi) conditions for TH17 differentiation. Assay was performed as described in eLife 2015; 4:e05920.
Figure 19:
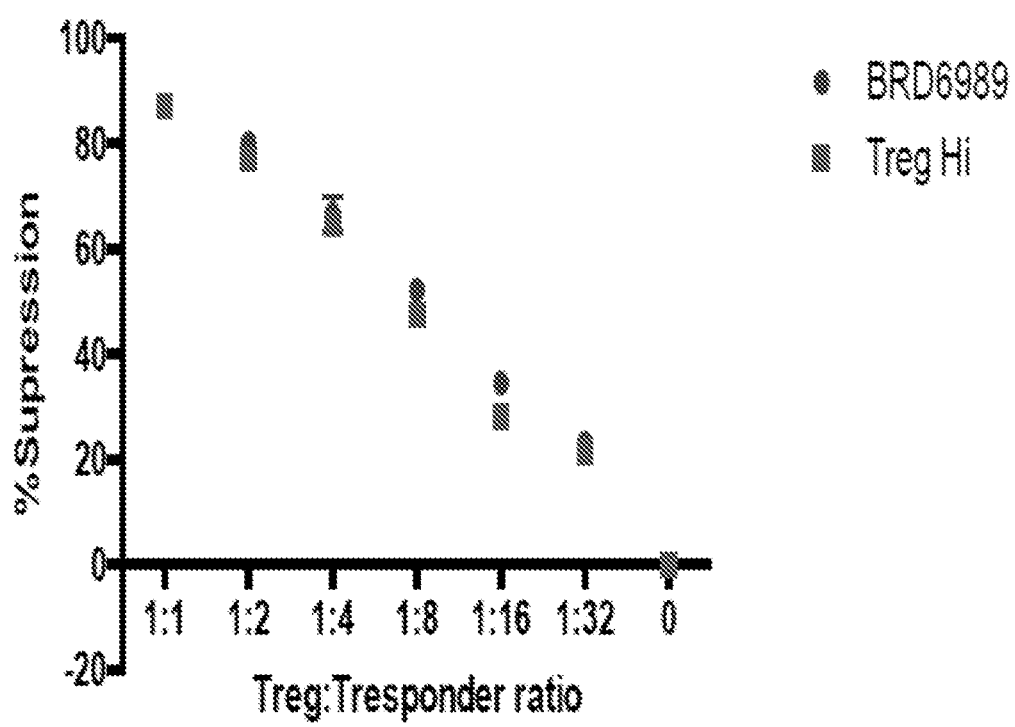
FIG. 19—Suppressing T-cell proliferation in vitro. $T_{reg}$ cells are co-cultured at increasing dilutions with CFSE-labeled responder CD4+ T cells and their ability to suppress responder T cell proliferation upon anti-CD3/CD28 stimulation is assessed. Naive CD4+ T cells from Foxp3IRES-GFP mice were cultured under either optimal conditions for $T_{reg}$ differentiation ($T_{reg}$ Hi) or sub-optimal $T_{reg}$ differentiation conditions in the presence of BRD6989. The resulting GFP+ Treg cells were sorted by FACS. Sorted Treg cells generated using either $T_{reg}$ hi conditions or in the presence of BRD6989 suppressed the proliferation of co-cultured responder CD4+ T cells in vitro at each dilution, indicating equal efficacy between both populations of $T_{reg}$ cells. Assay was performed as described in eLife 2015; 4:e05920.

Imbalances between anti-inflammatory (FoxP3+ Treg) and pro-inflammatory (TH1 and TH17) CD4+ T cell lineages can lead to pathogenic inflammations in a number of diseases contexts. Therapeutic strategies that enhance FoxP3+ Treg differentiation and/or function are being pursued for treatment of immune and inflammatory disorders. Treatment of naïve CD4+ T cells in the presence of multiple structural classes of CDK8 inhibitors can enhance differentiation into FoxP3+$T_{regs}$ (FIG. 16). Importantly, Treg enhancement occurs at compound concentrations that do not affect cell viability (FIG. 16). In addition, CDK8 inhibitors do not promote differentiation of naïve CD4+ T cells towards inflammatory TH1 and TH17 lineages (FIGS. 17 and 18). Finally, CDK8 inhibitor-induced $T_{reg}$ cells are capable of suppressive proliferation of naïve CD4+ T cells to a similar degree as $T_{reg}$s derived under standard culture conditions (high TGF-beta), which indicates that CDK8 inhibitor induced $T_{reg}$s are functional (FIG. 19).

Example 3

Figure 20:
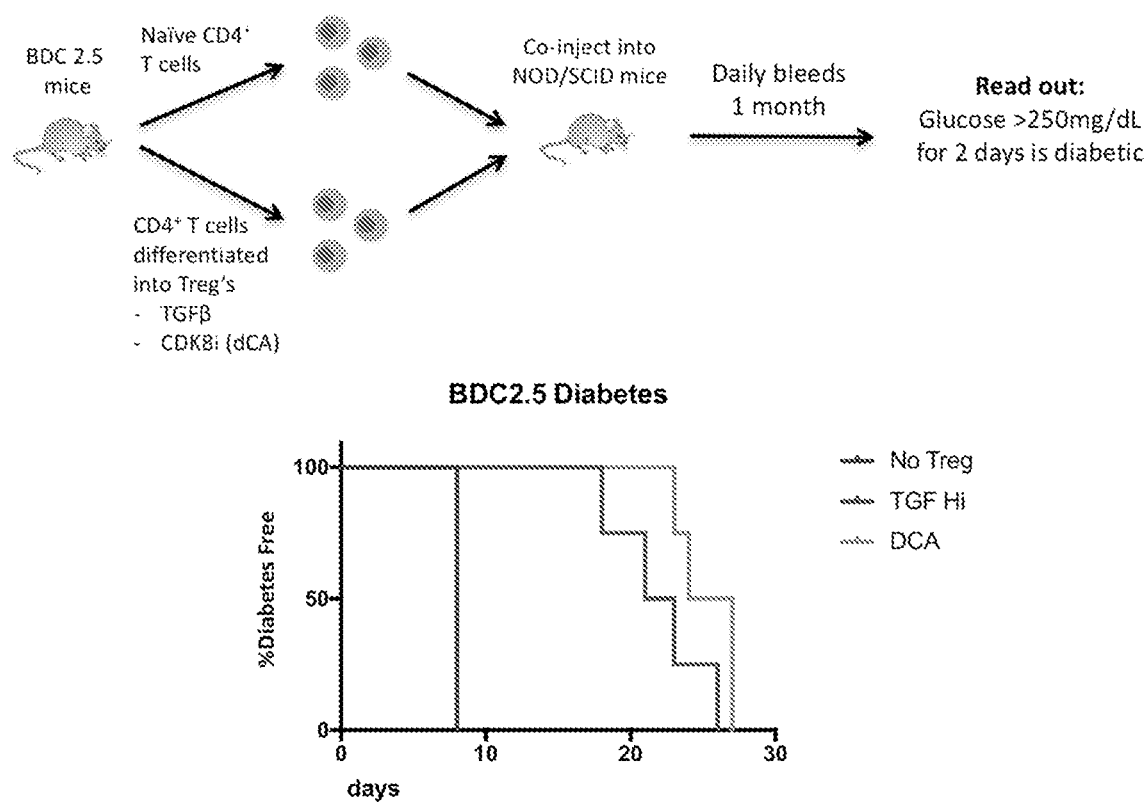
FIG. 20—T$_{regs}$ differentiated by CDK8 inhibition ex vivo are suppressive in a T-cell dependent diabetes model.

As previously described, $5 \times 10^4$ CD4$^+$CD62L$^+$ T cells isolated from NOD-BDC2.5 mice were administered intravenously to NOD-scid mice with or without $1 \times 10^5$ sorted $T_{reg}$ cells generated from NOD-BDC2.5, Foxp3$^{IRES-GFP}$ mice following ex vivo differentiation in the presence of CDK8 inhibitor (Herman et al. 2004; Tarbell et al. 2004). Blood glucose levels were measured with a handheld Contour glucometer (Bayer, Leverkusen, Germany) at days 3, 6, 8 and every day thereafter. Diabetes was diagnosed when blood sugar was over 250 mg/dl for 2 consecutive days. As show in FIG. 20, $T_{reg}$ differentiated by CDK8 inhibition ex vivo are suppressive in a T-cell dependent diabetes model.

REFERENCES CITED

1. Saraiva, M. & O'Garra, A. The regulation of IL-10 production by immune cells. *Nat Rev Immunol* 10, 170-81 (2010).
2. Shouval, D. S. et al. Interleukin 10 receptor signaling: master regulator of intestinal mucosal homeostasis in mice and humans. *Adv Immunol* 122, 177-210 (2014).
3. Asadullah, K., Sterry, W. & Volk, H. D. Interleukin-10 therapy—review of a new approach. *Pharmacol Rev* 55, 241-69 (2003).
4. Braat, H. et al. A phase I trial with transgenic bacteria expressing interleukin-10 in Crohn's disease. *Clin Gastroenterol Hepatol* 4, 754-9 (2006).
5. Galeazzi, M. et al. A phase D3 clinical trial with Dekavil (F8-IL10), an immunoregulatory 'armed antibody' for the treatment of rheumatoid arthritis, used in combination with methotrexate. *Isr Med Assoc J* 16, 666 (2014).
6. Rodriguez, M. et al. Polarization of the innate immune response by prostaglandin E2: a puzzle of receptors and signals. *Mol Pharmacol* 85, 187-97 (2014).
7. Martin, M., Rehani, K., Jope, R. S. & Michalek, S. M. Toll-like receptor-mediated cytokine production is differentially regulated by glycogen synthase kinase 3. *Nat Immunol* 6, 777-84 (2005).
8. Clark, K. et al. Phosphorylation of CRTC3 by the salt-inducible kinases controls the interconversion of classically activated and regulatory macrophages. *Proc Natl Acad Sci USA* 109, 16986-91 (2012).
9. Sundberg, T. B. et al. Small-molecule screening identifies inhibition of salt-inducible kinases as a therapeutic strategy to enhance immunoregulatory functions of dendritic cells. *Proceedings of the National Academy of Sciences of the United States of America* 111, 12468-12473 (2014).
10. Wang, B. et al. Microtubule acetylation amplifies p38 kinase signalling and anti-inflammatory IL-10 production. *Nat Commun* 5, 3479 (2014).
11. Na, Y. R. et al. The early synthesis of p35 and activation of CDK5 in LPS-stimulated macrophages suppresses interleukin-10 production. *Science Signaling* 8 (2015).
12. Souto, A. & Gomez-Reino, J. J. Apremilast for the treatment of psoriatic arthritis. *Expert Rev Clin Immunol* 11, 1281-90 (2015).
13. Gordon, J. N. et al. CC-10004 but not thalidomide or lenalidomide inhibits lamina propria mononuclear cell TNF-alpha and MMP-3 production in patients with inflammatory bowel disease. *Journal of Crohn's & Colitis* 3, 175-182 (2009).
14. Xing, L., Rai, B. & Lunney, E. A. Scaffold mining of kinase hinge binders in crystal structure database. *J Comput Aided Mol Des* 28, 13-23 (2014).
15. Allen, B. L. & Taatjes, D. J. The Mediator complex: a central integrator of transcription. *Nature Reviews Molecular Cell Biology* 16, 155-166 (2015).
16. Bancerek, J. et al. CDK8 Kinase Phosphorylates Transcription Factor STAT1 to Selectively Regulate the Interferon Response. *Immunity* 38, 250-262 (2013).
17. Shi, J. et al. Scalable Synthesis of Cortistatin A and Related Structures. *Journal of the American Chemical Society* 133, 8014-8027 (2011).
18. Pelish, H. E. et al. Mediator kinase inhibition further activates super-enhancer-associated genes in AML. *Nature* 526, 273-276 (2015).
19. Mallinger, A. et al. Discovery of Potent, Selective, and Orally Bioavailable Small-Molecule Modulators of the Mediator Complex-Associated Kinases CDK8 and CDK19. *Journal of Medicinal Chemistry* 59, 1078-1101 (2016).
20. Kwiatkowski, N. et al. Targeting transcription regulation in cancer with a covalent CDK7 inhibitor. *Nature* 511, 616-620 (2014).
21. Li, N. et al. Cyclin C is a haploinsufficient tumour suppressor. *Nature Cell Biology* 16, 1080-1091 (2014).
22. O'Connell, D. J. et al. Simultaneous Pathway Activity Inference and Gene Expression Analysis Using RNA Sequencing. *Cell Syst* 2, 323-34 (2016).
23. Garber, M. et al. A high-throughput chromatin immunoprecipitation approach reveals principles of dynamic gene regulation in mammals. *Mol Cell* 47, 810-22 (2012).
24. Witte, S., O'Shea, J. J. & Vahedi, G. Super-enhancers: Asset management in immune cell genomes. *Trends Immunol* 36, 519-26 (2015).
25. Shlyueva, D., Stampfel, G. & Stark, A. Transcriptional enhancers: from properties to genome-wide predictions. *Nature Reviews Genetics* 15, 272-286 (2014).
26. Porter, D. C. et al. Cyclin-dependent kinase 8 mediates chemotherapy-induced tumor-promoting paracrine activities. *Proc Natl Acad Sci USA* 109, 13799-804 (2012).
27. Poss, Z. C. et al. Identification of Mediator Kinase Substrates in Human Cells using Cortistatin A and Quantitative Phosphoproteomics. *Cell Rep* 15, 436-50 (2016).
28. Yamamoto, S. et al. Mediator cyclin-dependent kinases upregulate transcription of inflammatory genes in cooperation with NF-kappaB and C/EBPbeta on stimulation of Toll-like receptor 9. *Genes Cells* (2017).
29. Lin, A. et al. Casein kinase II is a negative regulator of c-Jun DNA binding and AP-1 activity. *Cell* 70, 777-89 (1992).
30. Huang, C. C. et al. Calcineurin-mediated dephosphorylation of c-Jun Ser-243 is required for c-Jun protein stability and cell transformation. *Oncogene* 27, 2422-9 (2008).
31. Taira, N. et al. DYRK2 priming phosphorylation of c-Jun and c-Myc modulates cell cycle progression in human cancer cells. *J Clin Invest* 122, 859-72 (2012).
32. Aikawa, Y. et al. Treatment of arthritis with a selective inhibitor of c-Fos/activator protein-1. *Nature Biotechnology* 26, 817-823 (2008).
33. Lim, S. H. & Kaldis, P. Cdks, cyclins and CKIs: roles beyond cell cycle regulation. *Development* 140, 3079-3093 (2013).
34. Saraiva, M. et al. Identification of a macrophage-specific chromatin signature in the IL-10 locus. *J Immunol* 175, 1041-6 (2005).
35. Donner, A. J., Ebmeier, C. C., Taatjes, D. J. & Espinosa, J. M. CDK8 is a positive regulator of transcriptional elongation within the serum response network. *Nat Struct Mol Blot* 17, 194-201 (2010).
36. Schreiber, S. et al. Safety and efficacy of recombinant human interleukin 10 in chronic active Crohn's disease. Crohn's Disease IL-10 Cooperative Study Group. *Gastroenterology* 119, 1461-72 (2000).
37. Marlow, G. J., van Gent, D. & Ferguson, L. R. Why interleukin-10 supplementation does not work in Crohn's disease patients. *World J Gastroenterol* 19, 3931-41 (2013).
38. Itakura, E. et al. IL-10 expression by primary tumor cells correlates with melanoma progression from radial to vertical growth phase and development of metastatic competence. *Mod Pathol* 24, 801-9 (2011).
39. Pyonteck, S. M. et al. CSF-1R inhibition alters macrophage polarization and blocks glioma progression. *Nat Med* 19, 1264-72 (2013).
40. Wang, S. et al. Expression of CD163, interleukin-10, and interferon-gamma in oral squamous cell carcinoma: mutual relationships and prognostic implications. *Eur J Oral Sci* 122, 202-9 (2014).
41. Clarke, P. A. et al. Assessing the mechanism and therapeutic potential of modulators of the human Mediator complex-associated protein kinases. *Elife* 5 (2016).
42. Yamaoka, K. Janus kinase inhibitors for rheumatoid arthritis. *Curr Opin Chem Biol* 32, 29-33 (2016).
43. Miller, S. C. et al. Identification of known drugs that act as inhibitors of NF-kappa B signaling and their mechanism of action. *Biochemical Pharmacology* 79, 1272-1280 (2010).
44. Herman et al. CD4+CD25+T regulatory cells dependent on ICOS promote regulation of effector cells in the pre-diabetic lesion. *The Journal of Experimental Medicine,* 199:1479-1489 (2004).
45. Tarbell et al. CD25+CD4+ T cells, expanded with dendritic cells presenting a single autoantigenic peptide, suppress autoimmune diabetes. *The Journal of Experimental Medicine,* 199:1467:1477.

What is claimed is:

1. A method for treating inflammation and/or autoimmune disease, comprising administering to a subject in need thereof a composition comprising a CDK8 inhibitor, wherein the CDK8 inhibitor is selected from

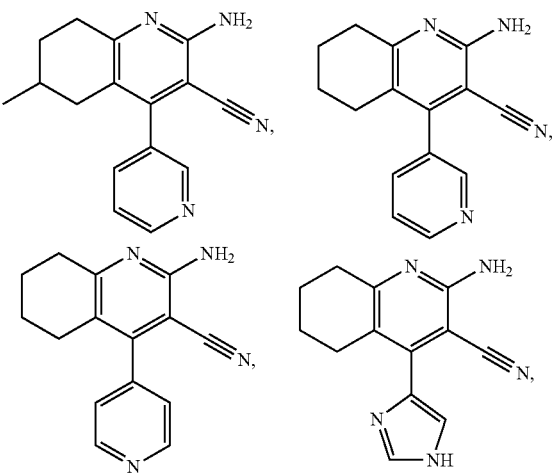

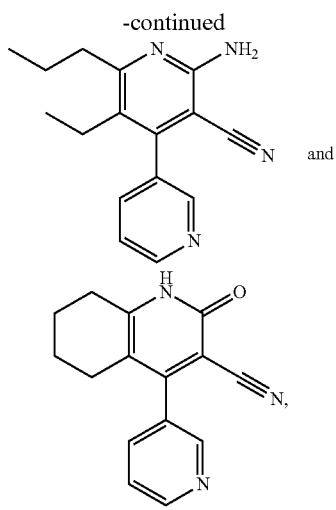

or a stereoisomer, racemic mixture, pharmaceutically acceptable salt, hydrate, or solvate thereof.

2. The method of claim 1, wherein the subject suffers from Addison's disease, agammaglobulinemia, alopecia areata, amyloidosis, ankylosing spondylitis, antig-GBM/anti-TBM nephritis, antiphospholipid syndrome, autoimmune hepatitis, autoimmune inner ear disease, axonal & neuronal neuropathy, Behcet's disease, bullous pemphigold, Castleman disease, celiac disease, Chagas disease, chronic inflammatory demyelinating polyneuropathy (CIDP), chronic recurrent multifocal osteomyelitis, Churg-Strauss, cicatrical pemphigold/benign mucosal pemphigold, Cogan's syndrome, cold agglutinin disease, congenital heart block, coxsackie myocarditis, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitits, giant cell arteritis (temporal arteritis), giant cell myocarditis, glomerulonephritis, Goodpasture's syndrome, granulomatosis with polyangitis, Grave's disease, Guillian-Barre syndrome, Hashimoto's thyroiditis, hemolytic anemia, Henoch-Schonnlien purpura, herpes gestationis or pemphigold gestationis, hypogammaglobulinemia, IgA nephropathy, IgG4-related sclerosing disease, inclusion body myositis, interstitial cystitis, juvenile arthritis, juvenile diabetes (Type 1 diabetes), juvenile myositis, Kawasaki disease, Lambert-Eaton syndrome, leukocytoclastic vasculitis, lichen planus, lichen sclerosis, ligneous conjunctivitis, linear IgA disease, lupus, lyme disease chronic, Meniere's disease, microscopic polyangiitis, mixed connective tissue disease, Mooren's ulcer, Mucha-Habermann disease, multiple sclerosis, myasthenia gravis, myositis, narcolepsy, neuromyelitis opica, neutropenia, ocular cicatrical pemphigold, optic neuritis, palindromic rheumatism, PANDAS (pediatric autoimmune neuropsychiatric disorders associated with *Streptococcus*), paraneoplastic cerebellar degeneration, paroxysmal nocturnal hemoglobinuria, Parry Romber syndrome, pars planitis (peripheral uveitis), Parsonnage-Turner syndrome, pemphigus, peripheral neuropathy, perivenous encephalomyelitis, pernicious anemia, POEMS syndrome, polyarteritis nodosa, polymyalgia rheumatic, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, Reiter's syndrome, relapsing polychondritis, restless leg syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic opthalmia, Takayasu's arteritis, temporal arteritis/giant cell arteritis, thrombocytopenic purpura, Tolosa-Hunt syndrome, transverse myelitis, ulcerative colitis, undifferentiated connective tissue disease, uveitis, vasculitis, vitiligo, and Wegner's granulomatosis (granulomatosis with polyangiitis).

3. The method of claim 2, wherein the subject suffers from an inflammatory bowel disease.

4. The method of claim 1, wherein the subject requires immunosuppression to prevent rejection following transplantation.

5. The method of claim 1, wherein the CDK8 inhibitor modulates innate immune activation comprising suppression of NF-κB or STAT1 pathway activity.

6. The method of claim 1, wherein the composition further comprises a pharmaceutically acceptable excipient and/or carrier.

7. The method of claim 1, wherein the CDK8 inhibitor is

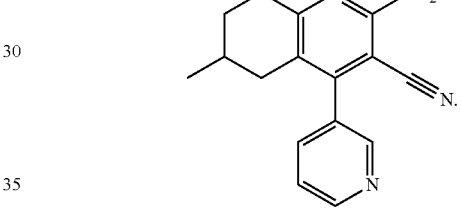

8. A method for treating inflammation and/or autoimmune disease, comprising administering to a subject in need thereof a composition comprising a CDK8 inhibitor, wherein the CDK8 inhibitor is $\Delta^{16}$-cortistatin A, or a stereoisomer, racemic mixture, pharmaceutically acceptable salt, hydrate, or solvate thereof.

9. The method of claim 8, wherein the subject suffers from Addison's disease, agammaglobulinemia, alopecia areata, amyloidosis, ankylosing spondylitis, antig-GBM/anti-TBM nephritis, antiphospholipid syndrome, autoimmune hepatitis, autoimmune inner ear disease, axonal & neuronal neuropathy, Behcet's disease, bullous pemphigold, Castleman disease, celiac disease, Chagas disease, chronic inflammatory demyelinating polyneuropathy (CIDP), chronic recurrent multifocal osteomyelitis, Churg-Strauss, cicatrical pemphigold/benign mucosal pemphigold, Cogan's syndrome, cold agglutinin disease, congenital heart block, coxsackie myocarditis, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitits, giant cell arteritis (temporal arteritis), giant cell myocarditis, glomerulonephritis, Goodpasture's syndrome, granulomatosis with polyangitis, Grave's disease, Guillian-Barre syndrome, Hashimoto's thyroiditis, hemolytic anemia, Henoch-Schonnlien purpura, herpes gestationis or pemphigold gestationis, hypogammaglobulinemia, IgA nephropathy, IgG4-related sclerosing disease, inclusion body myositis, interstitial cystitis, juvenile arthritis, juvenile diabetes (Type 1 diabetes), juvenile myositis, Kawasaki disease, Lambert-Eaton syndrome, leukocytoclastic vasculitis, lichen planus, lichen sclerosis, ligneous conjunctivitis, linear IgA disease, lupus, lyme disease chronic, Meniere's disease, microscopic polyangiitis, mixed connective tissue disease, Mooren's ulcer, Mucha-Habermann disease, multiple sclerosis, myasthenia gravis, myositis, narcolepsy, neuromyelitis opica, neutropenia, ocular cicatrical pemphigold, optic neuritis, palindromic rheumatism, PANDAS (pediatric autoimmune neuropsychiatric disorders associated with *Streptococcus*), paraneoplastic cerebellar degeneration, paroxysmal nocturnal hemoglobinuria, Parry Romber syndrome, pars planitis (peripheral uveitis), Parsonnage-Turner syndrome, pemphigus, peripheral neuropathy, perivenous encephalomyelitis, pernicious anemia, POEMS syndrome, polyarteritis nodosa, polymyalgia rheumatic, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, Reiter's syndrome, relapsing polychondritis, restless leg syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic opthalmia, Takayasu's arteritis, temporal arteritis/giant cell arteritis, thrombocytopenic purpura, Tolosa-Hunt syndrome, transverse myelitis, ulcerative colitis, undifferentiated connective tissue disease, uveitis, vasculitis, vitiligo, and Wegner's granulomatosis (granulomatosis with polyangiitis).

10. The method of claim 9, wherein the subject suffers from an inflammatory bowel disease.

11. The method of claim 8, wherein the subject requires immunosuppression to prevent rejection following transplantation.

12. The method of claim 8, wherein the composition further comprises a pharmaceutically acceptable excipient and/or carrier.

* * * * *

UNITED STATES PATENT AND TRADEMARK OFFICE
CERTIFICATE OF CORRECTION

PATENT NO. : 11,285,144 B2
APPLICATION NO. : 16/323227
DATED : March 29, 2022
INVENTOR(S) : Thomas Sundberg et al.

Page 1 of 2

It is certified that error appears in the above-identified patent and that said Letters Patent is hereby corrected as shown below:

In the Specification

In Column 3, Line 12, delete "BRD03330" and insert -- BRD0330 --.

In Column 5, Line 15, delete "15 min 4 hr" and insert -- 15 min - 4 hr --.

In Column 5, Line 16, delete "Benjamin-" and insert -- Benjamini- --.

In Column 5, Line 31, delete "15 min 4 hr" and insert -- 15 min - 4 hr --.

In Column 5, Line 33, delete "Benjamin-" and insert -- Benjamini- --.

In Column 9, Line 65, delete "$T_{reg}$cells." and insert -- $T_{reg}$ cells. --.

In Column 9, Line 65, delete "nave" and insert -- naïve --.

In Column 10, Line 1, delete "nave" and insert -- naïve --.

In Column 12, Line 47, delete "U.S. Pat. No. 2,012,109" and insert -- US, 2012, 109 --.

In Column 17, Line 57, delete "nave" and insert -- naïve --.

In Column 20, Line 7, delete "0.3 5 μm," and insert -- 0.35 μm, --.

In Column 30, Line 64, delete "A-" and insert -- Δ- --.

In Column 31, Line 37, delete "50%" and insert -- ~50% --.

In Column 32, Line 52, delete "2 hours" and insert -- ~2 hours --.

Signed and Sealed this
Second Day of August, 2022

Katherine Kelly Vidal
*Director of the United States Patent and Trademark Office*

In Column 33, Line 23, delete "AP1" and insert -- AP-1 --.

In Column 34, Line 41, delete "1110" and insert -- Il-10 --.

In Column 34, Line 51, delete "A-P1" and insert -- AP-1 --.

In Column 35, Line 64, delete "FoxP3+T$_{regs}$" and insert -- FoxP3+ T$_{regs}$ --.

In Column 36, Line 37, delete "D3" and insert -- IB --.

In Column 36, Line 61, delete "CDKS" and insert -- CDK5 --.

In Column 38, Line 7, delete "Blot" and insert -- Biol --.

In Column 38, Line 34, delete "CD4+CD25+T" and insert -- CD4+CD25+ T --.